United States Patent [19]
Feng et al.

[11] Patent Number: 5,770,419
[45] Date of Patent: Jun. 23, 1998

[54] MUTANTS OF MYCELIOPHTHORA LACCASE WITH ENHANCED ACTIVITY

[75] Inventors: Xu Feng, Woodland; Randy M. Berka; Jill Angela Wahleithner, both of Davis, all of Calif.

[73] Assignee: Novo Nordisk Biotech, Inc., Davis, Calif.

[21] Appl. No.: 706,037

[22] Filed: Aug. 30, 1996

[51] Int. Cl.$^6$ .................................................... C12N 9/02

[52] U.S. Cl. ................ 435/189; 435/252.3; 435/252.33; 435/254.1; 435/255.1; 435/320.1; 435/256.1; 536/23.1; 536/23.2; 536/23.7; 536/23.74

[58] Field of Search .................................... 435/189, 69.1, 435/254.2, 254.3, 252.1, 252.3, 252.33, 320.1, 254.1, 255.1, 256.1; 536/23.1, 23.2, 23.74, 23.7

[56] References Cited

FOREIGN PATENT DOCUMENTS

| 0 506 431 A1 | 3/1992 | European Pat. Off. . |
| WO 92/01046 | 1/1992 | WIPO . |
| WO 95/07988 | 3/1995 | WIPO . |
| WO 95/33836 | 12/1995 | WIPO . |

OTHER PUBLICATIONS

Germann, Ursula A. et al., "Characterization Of Two Allelic Forms of Neurospora Crassa Laccase", 1988 by The American Society For Biochemistry And Molecular Biology, Inc., Jan. 15, vol. 263, No. 2, pp. 885–896.

Kojima Yasushi et al., "Cloning, Sequence Analysis, and Expression of Ligninolytic Phenoloxidase Genes of the White–rot Basidiomycete Coriolus", 1990 by The American Society of Biochemistry And Molecular Biology, vol. 265, No. 25, Sep. 5, pp. 15224–15230.

Askwith, Candice et al., "The FET3 Gene of *S. Cerevisiae* Encodes A Multicopper Oxidase Required For Ferrous Iron Uptake", Jan. 28 1994 by Cell Press, vol. 76, pp. 403–410.

Messerschmidt et al. "X–ray crystal structure of the Blue oxidase, Ascorbate oxidase from zucchini" J. Mol. Biol. 206, 513–529, 1989.

Messerschmidt et al. "Refined crystal structure of ascorbate oxidase at 1.9 A resolution" J. Mol. Biol. 224, 179–205, 1992.

Xu et al. "A study of a series of recombinant fungal lacacases and bilirubin oxidase that exhibit significant differences in redox potential, substrate specificity and stability" Biochem. Biophys. Acta 1292, 303–311, 1996.

Xu, F. "Oxidation of phenols, anilines, and benzenethiols by fungal laccases: Correlation between activity and redox potentials as well as halide inhibition" Biochemistry 35, 7607–7614, 1996.

*Primary Examiner*—Robert A. Wax
*Assistant Examiner*—Nashaat T. Nashed
*Attorney, Agent, or Firm*—Steve T. Zelson; James H. Harrington

[57] ABSTRACT

The present invention relates to mutants of a blue multi-copper oxidase, comprising (a) a substitution of one or more amino acid residues with other amino acid residues, (b) an insertion of one or more amino acid residues and/or (c) a deletion of one or more amino acid residues, wherein the substitution, insertion or deletion is carried out at a position which is located no greater than 15 Å from a Type I (T1) copper site. The present invention also relates to nucleic acid constructs comprising a nucleic acid sequence encoding the mutants of the present invention, host cells comprising the construct of the present invention, and methods for producing mutants of the present invention.

18 Claims, 20 Drawing Sheets

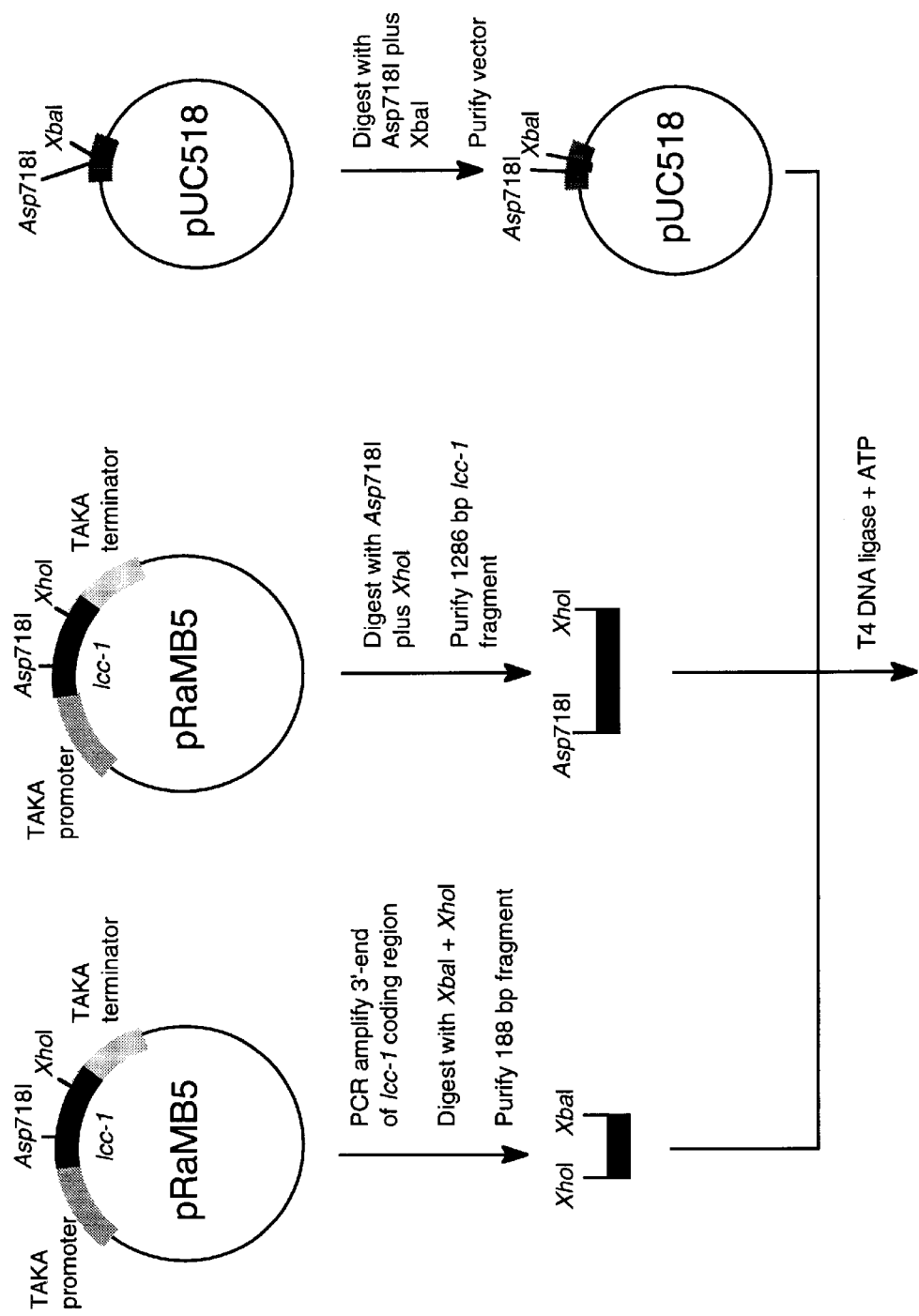

```
                87          96         105         114         123         132
ATG  CTT  TCT  AGC  ATT  ACC  CTC  CTA  CCT  TTG  CTC  GCT  GTC  TCA  ACC  CCC  GCC
 M    L    S    S    I    T    L    L    P    L    L    A    V    S    T    P    A 141         150         159         168         177         186
TTT  GCT  GCC  GTC  CGC  AAC  TAT  AAG  TTC  GAC  ATC  AAG  AAC  GTC  AAT  GTC  GCT  CCC
 F    A    A    V    R    N    Y    K    F    D    I    K    N    V    N    V    A    P 195         204         213         222         231         240
GAT  GGC  TTT  CAG  CGC  TCT  ATC  GTC  TCC  GTC  AAC  GGT  TTA  GTT  CCT  GGC  ACG  TTG
 D    G    F    Q    R    S    I    V    S    V    N    G    L    V    P    G    T    L 249         258         267         276         285         294
ATC  ACG  GCC  AAC  AAG  GAC  ACC  GCC  ACA  TTG  CGC  ATT  CAT  GTC  ACG  CAA  CTC  ACG
 I    T    A    N    K    D    T    A    T    L    R    I    H    V    T    Q    L    T 303         312         321         330         339         348
GAT  GGC  AGT  ATG  CGT  GCC  ACA  ACC  GCC  ATT  CAT  TGG  CAT  GGA  TTG  TTC  CAA  GCT
 D    G    S    M    R    A    T    T    A    I    H    W    H    G    L    F    Q    A 357         366         375         384         393         402
GAC  CCT  AGT  GAC  GAG  GAT  GGC  CCC  GCA  TTC  GTC  ACG  CAA  TGC  CCT  ATT  GCG  CAA
 D    P    S    D    E    D    G    P    A    F    V    T    Q    C    P    I    A    Q
```

Fig. 6A

```
                411             420             429             438             447             456
AAT TTG TCC     TAT ACA GAG     ATC CCA TTG     CGC GGC CAA     ACA GGA ACC     ATG TGG
 N   L   S       Y   T   E       I   P   L       R   G   Q       T   G   T       M   W 465             474             483             492             501             510
TAT CAC GCC     CAT CTT GCG     AGT CAA TAT     GTC GAT TTG     CGA GGC CCT     TTG GTC
 Y   H   A       H   L   A       S   Q   Y       V   D   L       R   G   P       L   V 519             528             537             546             555             564
ATC TAT GAT     CCA AAC AGT     CAA AAG TCG     CGC TAC GAC     GTG GAT GCG     GAT AGC
 I   Y   D       P   N   S       Q   K   S       R   Y   D       V   D   A       D   S 573             582             591             600             609             618
ACA GTC ATG     CTT GAG GAC     TGG TAC CAT     ACT CCA GCA     CCC GTT CTA     GAA AAG
 T   V   M       L   E   D       W   Y   H       T   P   A       P   V   L       E   K 627             636             645             654             663             672
CAA ATG TTC     TCG ACT AAT     AAC ACC GCT     CTG CTC TCT     CCT GTT CCG     GAC TCG GGT
 Q   M   F       S   T   N       N   T   A       L   L   S       P   V   P       D   S   G 681             690             699             708             717             726
CTT ATC AAT     GGC AAA GGG     CGC TAT GTG     GGC GGT CCC     GCA GTT CCC     CGG TCA GTA
 L   I   N       G   K   G       R   Y   V       G   G   P       A   V   P       R   S   V
```

Fig. 6B

```
             735           744           753           762           771           780
ATC AAC GTA AAA CGT GGG AAA CGA TAT CGC TTG GTA ATC AAC GCT TCT GCT
 I   N   V   K   R   G   K   R   Y   R   L   V   I   N   A   S   A 789           798           807           816           825           834
ATC GGG TCG TTT ACC TTT TCG ATC GAA GGA CAT AGT CTG ACT GTC ATT GAG GCC
 I   G   S   F   T   F   S   I   E   G   H   S   L   T   V   I   E   A 843           852           861           870           879           888
GAT GGG ATC CTG CAC CAG CCC TTG GAA GGA CAT GCT GTT GAC AGC TTC CAG TAC ATT GGA
 D   G   I   L   H   Q   P   L   E   G   H   A   V   D   S   F   Q   Y   I   G 897           906           915           924           933           942
CAA CGC TAC TCT GTC ATC GTT GAA GCA GGA ACC GCC AAC CAA AAC AGC TTC CAG TAC GCT ATT
 Q   R   Y   S   V   I   V   E   A   G   T   A   N   Q   N   S   F   Q   Y   A   I 951           960           969           978           987           996
CGT GCA CCA ATG ACC GTT GCA GGA GCC GGA ACC GCG AAT GCA AAC TTG GAC TAC TGG ACC
 R   A   P   M   T   V   A   G   A   G   T   A   N   A   N   L   D   Y   W   T 1005          1014          1023          1032          1041          1050
AAT GTC TTT GCC GTA TTG CAC TAC GAG GGA GCG CCC AAC GCC AAC GAA CCC ACG ACG
 N   V   F   A   V   L   H   Y   E   G   A   P   N   A   N   E   P   T   T
```

Fig. 6C

```
      1059            1068            1077            1086            1095            1104
GAA CAA GGC AGT GCT ATC GGT ACT GCA CTC GTT GAA GAG AAC CTC CAT GCG CTC
 E   Q   G   S   A   I   G   T   A   L   V   E   E   N   L   H   A   L 1113            1122            1131            1140            1149            1158
ATC AAC CCT GGC GCT CCT GGC GGC TCC GCT CCC GCA GAC GTT TCC CTC AAT CTT
 I   N   P   G   A   P   G   G   S   A   P   A   D   V   S   L   N   L 1167            1176            1185            1194            1203            1212
GCA ATT GGG CGC AGC ACA GTT GAT GGG ATT CTT AGG TTC ACA TTT AAT AAC ATC
 A   I   G   R   S   T   V   D   G   I   L   R   F   T   F   N   N   I 1221            1230            1239            1248            1257            1266
AAG TAC GAG GCT CCT TCG TTG CCC ACG CTC TTG AAG ATT CTT GCA TTT GCA GCG
 K   Y   E   A   P   S   L   P   T   L   L   K   I   L   A   F   A   A 1275            1284            1293            1302            1311            1320
AGC AAT GAC GCC GAT TTC ACG CCA AAT GAG CAC ACT ATC GTA TTG AAC AAT AAT
 S   N   D   A   D   F   T   P   N   E   H   T   I   V   L   N   N   N 1329            1338            1347            1356            1365            1374
AAA GTT ATC GAG CTC AAT ATC ACC GGA GGT GCA GAC CAC CCT ATC CAT CTC CAC
 K   V   I   E   L   N   I   T   G   G   A   D   H   P   I   H   L   H
```

Fig. 6D

```
            1383      1392      1401      1410      1419      1428
GGC CAT GTG TTT GAT ATC GTC AAA TCA CTC GGT GGT ACC CCG AAC TAT GTC AAC
 G   H   V   F   D   I   V   K   S   L   G   G   T   P   N   Y   V   N 1437      1446      1455      1464      1473      1482
CCG CCA CGC AGG GAC GTA CGT GTC GGA GGC ACC GGT GTG CTC CGA TTC
 P   P   R   R   D   V   R   V   G   G   T   G   V   L   R   F 1491      1500      1509      1518      1527      1536
AAG ACC GAT AAC CCA GGC CCA TGG TTT GTT CAC ATT GAC TGG CAC TTG
 K   T   D   N   P   G   P   W   F   V   H   I   D   W   H   L 1545      1554      1563      1572      1581      1590
GAG GCT GGG CTC GCA CTT GTC TTT GCC GAG GCC CCC AGC CAG ATT CGC CAG GGT
 E   A   G   L   A   L   V   F   A   E   A   P   S   Q   I   R   Q   G 1599      1608      1617      1626      1635      1644
GTC CAG TCG GTC CAG CCC AAC AAT GCC TGG AAC CAG CTC TGC CCC AAG TAC GCG
 V   Q   S   V   Q   P   N   N   A   W   N   Q   L   C   P   K   Y   A 1653      1662
GCT CTT CCT CCC GAT TTG CAG T
 A   L   P   P   D   L   Q   *
```

Fig. 6E

```
gctagcttcttggtcaccgtcgtttcgcccgcccctcctcttcaacccctgagtagtcggctaagcgatcctca          80 atctggtcttgtgaggtcacgtcctccagcagatgacagttcatcgagcgagtgatctccaccaccagaagggagggg      160 gatgcgcgcatgctccaacatccctgtgtgtcgctagagacgtcgcggcatcagccttttcatcacaccgagcacgtccac   240 ggaccggctcctttcaccccgcgtcctccggaggattgagtcacgatatttcgggatgtgggaaggggagagaaagga      320 gggggaggggcggaaacatgttggatacgagctgcgccccttttcaacatcgagaacaggaagtcgttggtgtcggcc      400 gtaatgtctataaacgaggctccttctctcgactgtctcaggttctctctcgtccacaccaagccagtcttg            480 cctgagccacctgagccacctcaactcatcatcttcagtcaagtcgttcattgacattgtgtctctttctatcgagt       560 cggcttcccggcccttcaccacaacATGAAGTCCTTCATCAGCGCCGACGCTTTTGGTGGGCATTCTCACCCCTAGCG      640
                         MetLysSerPheIleSerAlaAspAlaPheGlyGlyHisSerHisProSerV        -29

TTGCTGCTGCCCCTCCATCCACCCCTGAGCAGCGCGACCTGCTCGTCCCGATCACGGAGAGGAGGCAGCCGTGAAG        720
alaAlaAlaAlaProProSerThrProGluGlnArgAspLeuLeuValProIleThrGluArgGluAlaAlaValLys        -3

GCTCGCCAGCAGAGTGCAAACACCCCAGCAACCGGCGTGCTGACTGACGGATACGACATCAACACCGACTACGAAGT       800
AlaArgGlnGlnSerCysAsnThrProSerAsnArgAlaCysTrpThrAspGlyTyrAspIleAsnThrAspTyrGluVa      25
```

Fig. 7A

```
GGACAGCCCGGACACGGGTGTGTTCGGCCGgtgagtgctctcgttaattacgcttcggcgagttgcgcagatattaa    880
lAspSerProAspThrGlyValValArgPro                                                   35 atactgcaaacctaagcaggagctgacatgcgacagTACACTCTGACTCTCCACCGAAGTGACAACTGGACCGGACCTGA  960
                                    TyrThrLeuThrGluValAlaAspAsnTrpThrGlyProAs    50

TGGCGTCGTCAAGGAGAAGGTCATGCTGGTTAACAgtacggcacccctttctgtcctaggatctgggtgatgtgcgtc   1040
pGlyValValLysGluLysValMetLeuValAsnA                                               62 gttgccctgagagagactgaccgagccttggctgtgcagATAGTATAATCGgtaattaattatacgccctgcctccagc  1120
                                       snSerIleIleG                              66 agccccagcagctcgagaagggtatctgaagttagtcaggcctgacctgaccgggccaacccaccatagGACCAAC     1200
                                                                     lyProTh      68

AATCTTTGCGGACTGGGGCGACACGGTCATCAACAACCTCGAGACCAACGGgtatgtctgtgcttgc              1280
rIlePheAlaAspTrpGlyAspThrValIleGlnValThrAsnLeuGluThrAsnGl                         89 tctcttgctctcctcgtccgcgactaataatatcaactcgtgtggaaaacagCACGTCGATCCACTGGCACGGACTG    1360
                                                     yThrSerIleHisTrpHisGlyLeu    97
```

Fig. 7B

```
CACCAGAAGGGCACCAACCTGCACGACGGCGCCAACGGTATCACCGAGTGCCCGATCCCGCCCAAGGGAGGAGGAAGGT      1440
HisGlnLysGlyThrAsnLeuHisAspGlyAlaAsnGlyIleThrGluCysProIleProProLysGlyGlyArgLysVa      124

GTACCGGTTCAAGGCTCAGCAGTACGGACGAGCTGGTACCACTCTCGGCCACTTCTCGCCAGTACGGCAACGGCGTGGTCG      1520
lTyrArgPheLysAlaGlnGlnTyrGlyThrSerTrpTyrHisSerHisPheSerAlaGlnTyrGlyAsnGlyValValG      151

GGGCCATTCAGATCAACGGGCCCTCGCTGCCGTACGACACCGACCTGGGCGTGTTCCCCATCAGCGACTACTACTAC        1600
lyAlaIleGlnIleAsnGlyProAlaSerLeuProTyrAspThrAspLeuGlyValPheProIleSerAspTyrTyrTyr     177

AGCTCGGCCGACGAGCTGGTGGAACTCACCAAGAACTCGGGCGCCCTTCAGCGACAACGTCCTGTTCAACGGCACGGC       1680
SerSerAlaAspGluLeuValGluLeuThrLysAsnSerGlyAlaProPheSerAspAsnValLeuPheAsnGlyThrAl      204

CAAGCACCCCGGAGACGGCGAGGGCGAGTACGCCAACGTGACGCTCACCCCGGGCCACCGCCCTGCGCCTGATCA          1760
aLysHisProGluThrGlyGluGlyGluTyrAlaAsnValThrLeuThrProGlyArgArgHisArgLeuIleA             231

ACACGTCGGTCGAGAACACCTTCCAGGTCTCGCTCGTCAACCACCATGACCATCATCGCCGCCGACATGGTGCCCGTC       1840
snThrSerValGluAsnThrPheGlnValSerLeuValAsnHisThrMetThrIleIleAlaAlaAspMetValProVal      257

AACGCCATGACGGTCGACAGCCTCTTCCTCGGCGTCGGCCAGCGCTACGATGTCGTCATCGAAGCCAGCCGAACGCCCGG     1920
AsnAlaMetThrValAspSerLeuPheLeuGlyValGlyGlnArgTyrAspValValIleGluAlaSerArgThrProGl      284
```

Fig. 7C

```
GAACTACTGGTTTAACGTCACATTTGGCGGGGGCCTGCTCTGCGGGCGGCTCCAGGAATCCCTACCCGGCCGCCATCTTCC    2000
 yAsnTyrTrpPheAsnValThrPheGlyGlyGlyLeuLeuCysGlyLeuCysGlyGlySerArgAsnProTyrProAlaAlaIlePheH    311

ACTACGCCCGGCGCCCCCGGCGGGGGCCCGCCACGGACGAGGGCAAGGCCCCCGGTCGACCACAACTGCCTGGACCTCCCCAAC    2080
 isTyrAlaGlyAlaProGlyAlaProGlyGlyProProThrAspGluGlyLysAlaProValAspHisAsnCysLeuAspLeuProAsn    337

CTCAAGCCCCGTCGTGGCCCGACGTGCCCCTGAGCGGCTTCGCCAAGGCGGCCGACAACACGCTCGACGTCACCCTCGA    2160
 LeuLysProValValAlaAlaArgaspValProLeuSerGlyPheAlaLysArgProAspAsnThrLeuAspValThrLeuAs    364

CACCACGGGCACGCCCCCTGTTCGTCTGGAAGGTCAACGGCAGCGCCATCAACATGACTGGGCAGGCCCGTCGTCGACT    2240
 pThrThrGlyThrProLeuPheValTrpLysValAsnGlySerAlaIleAsnIleAspTrpGlyArgProValValAspT    391

ACGTCCTCACGCAGAACACCAGCTTCCCACCCGGGTACAACATTGTCGAGGTGAACGGAGCTGATCAGgtaagaaaaagg    2320
 yrValLeuThrGlnAsnThrSerPheProProGlyTyrAsnIleValGlyValAsnGlyAlaAspGln    413 ggaccgcaggggtgctgctgcaagtacacacctgctcgccctcctgttcctttcctaataactacctcccaaccctccccccc    2400 taattaattcactttaaaggccgatcaagactgaccgagcccccctctcctttgcagTGGTCGTACTGGTTGATCGAGAACG    2480
                                                          TrpSerTyrTrpLeuIleGlnAsnA    422
```

Fig. 7D

```
ATCCCGGGGCACCTTTCACCCTACCGCATCCGATGCACCTGCACgtaagttggatacatatatatatatatacatt    2560
spProGlyAlaProPheThrLeuProHisProMetHisLeuHis                                     436 gctttcctggctcgctccctaaataaattaaataacaaaataacaaaaataaagGGCCACGACTTTTACGTGCTGGG    2640
                                                      GlyHisAspPheTyrValLeuGl   444

CCGCTCGCCCGACGAGTCGCCGGCATCCAACGAGCGGCACGTGTTCGATCCGGCGGGGACGCGGGCCTGCTGAGCGGGG   2720
yArgSerProAspGluSerProAlaSerAsnGluArgHisValPheAspProAlaArgAspAlaGlyLeuLeuSerGlyA   471

CCAACCCCTGTGCGGGGACGATGCTGCCGGCGTTCGGGTGGTGGTGCTGGCCTTCCGGGCCGACAACCCGGGC          2800
laAsnProValArgArgAspValSerMetLeuProAlaPheGlyTrpValValLeuAlaPheArgAlaAspAsnProGly   497

GCCTGGCGTGTTCCACTGCCACATCGCCTGGCACGTCTCGGGCGCCCTGGGCGTCGTCTACCTCGAGCGCCGACGACCT   2880
AlaTrpLeuPheHisCysHisIleAlaTrpHisValSerGlyGlyLeuGlyValValValTyrLeuGluArgAlaAspLe   524

GCGCGGGGCGTCTCGACGCCCTCTGCGCCGACTGGCGCGCTACTGGCCTACCAACC                          2960
uArgGlyAlaValSerAspAlaAspAlaAspAspAspAspLeuAspAspArgLeuCysAlaAspTrpArgArgTyrTrpProThrAsnP   551

CCTACCCCAAGTCCGACTCGGGCCTCAAGCACCGCTGGGTCGAGGAGGGCGAGTGGCTGGTCAAGGCGTgtgagcgaaggag   3040
roTyrProLysSerAspSerGlyLeuLysHisArgTrpValGluGluGlyGluTrpLeuValLysAla***
```

Fig. 7E gaaaaaggaaacaaagaggggggggctagttcctattttgctttttgtcttgtccttgtgctggcggt 3120 taccctggtaaaggagaagggggccccaagttcgagtgggtgtgatcgggtaaatattatcaagagatct 3192

Fig. 7F 5,770,419

MUTANTS OF MYCELIOPHTHORA LACCASE WITH ENHANCED ACTIVITY

BACKGROUND OF THE INVENTION

1. Field of the Invention

The present invention relates to mutant multi-copper oxidases. More specifically, the invention relates to oxidases which have been modified so as to exhibit altered pH activity profiles relative to the wild-type oxidase.

2. Description of the Related Art

There are currently a number of well-known blue copper oxidases which have various commercial/industrial applications. Two major classes of these enzymes are recognized: (1) the single copper proteins, which are single copper-containing, blue electron-transfer proteins such as plastocyanin, azurin, stellacyanin, amicyanin, auracyanin, cucumber basic blue, mavicyanin, rusticyanin, and umecyanin; and (2) the multi-copper oxidases, which are multiple copper-containing, blue oxidoreductases such as laccase, bilirubin oxidase, phenoxazinone synthase, ascorbate oxidase, ceruloplasmin, and nitrite reductase. The blue color of these proteins arises from the so-called Type 1 (T1) copper site.

It is an object of the present invention to provide mutants of blue multi-copper oxidases which have improved properties.

BRIEF DESCRIPTION OF THE FIGURES

FIG. 6 shows the nucleotide sequence and the deduced amino acid sequence of *Rhizoctonia solani* laccase isozyme 4 (rsl4) gene (SEQ ID NOS:24 and 25).

FIG. 7 shows the nucleotide sequence and the deduced amino acid sequence of *Myceliophthora thermophila* laccase lcc-1 gene (SEQ ID NOS:26 and 27).

SUMMARY OF THE INVENTION

Figure 1B:
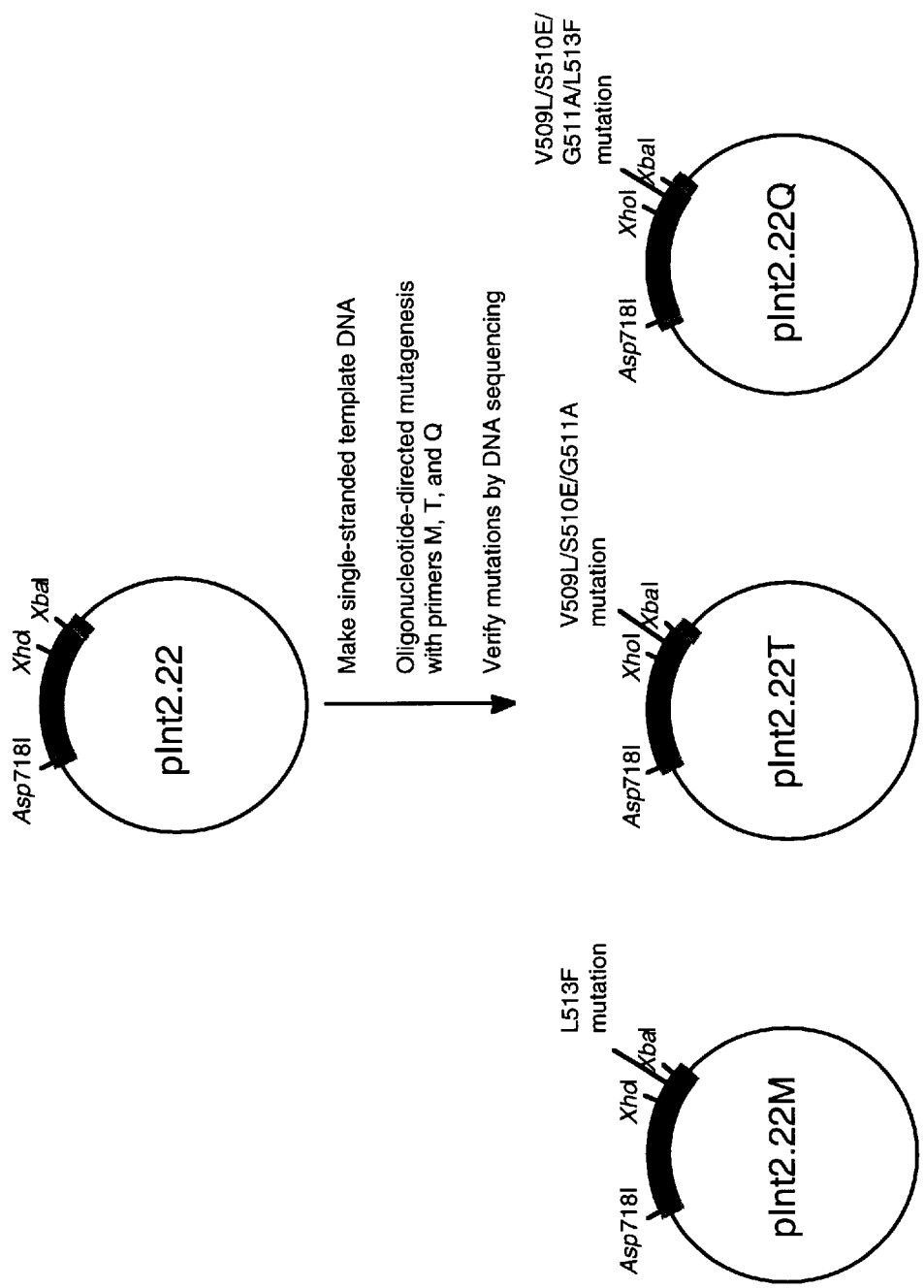
FIG. 1 shows the scheme for construction of intermediate plasmid pInt2.22 and oligonucleotide-directed mutagenesis of the *Myceliophthora thermophila* lcc-1 gene.

The present invention relates to mutants of a blue multi-copper oxidase, comprising a mutation selected from the group consisting of (a) a substitution of one or more amino acid residues with other amino acid residues, (b) an insertion of one or more amino acid residues and/or (c) a deletion of one or more amino acid residues, wherein the substitution, insertion or deletion is carried out at a position which is located no greater than 15 Å from a Type I (T1) copper site. The present invention also relates to nucleic acid constructs comprising a nucleic acid sequence encoding the mutants of the present invention, host cells comprising the construct of the present invention, and methods for producing mutants of the present invention.

DETAILED DESCRIPTION OF THE INVENTION

The present invention relates to mutants of a blue multi-copper oxidase, comprising (a) a substitution of one or more amino acid residues with other amino acid residues, (b) an insertion of one or more amino acid residues and/or (c) a deletion of one or more amino acid residues, wherein the substitution, insertion or deletion is carried out at a position which is located no greater than 20 Å from a Type I (T1) copper site. Preferably, each mutation is a substitution of one or more amino acid residues with other amino acid residues.

The Type 1 copper site consists of four ligands which bind to a copper ion, each of which is either an amino acid residue of the blue copper oxidase or a small molecule such as a water molecule. A ligand is defined herein an amino acid residue of a blue copper oxidase which binds to a copper ion. The Type 1 copper site of all known blue copper oxidases consists of the following ligands: two histidines (H), one cysteine (C), and, possibly, one additional methionine.

The ligand location for *Rhizoctonia solani* is: H 427, C 480, H 485 and possibly L 470 and for *Myceliophthora thermophilum* is H 431, C 503, H 508 and possibly L 513.

For purposes of the present invention, the distance from a Type I copper site is measured from the copper ion.

In a preferred embodiment, the mutant has a mutation at a position which is located no greater than 15 Å from a Type I copper site. In another preferred embodiment, the mutant has a mutation at a position which is located no greater than 12 Å from a Type I copper site. In another preferred embodiment, the mutant has a mutation at a position which is located no greater than 10 Å from a Type I copper site. In another preferred embodiment, the mutant has a mutation at a position which is located no greater than 8 Å from a Type I copper site. In another preferred embodiment, the mutant has a mutation at a position which is located no greater than 6 Å from a Type I copper site. In another preferred embodiment, the mutant has a mutation at a position which is located no greater than 4 Å from a Type I copper site. In another preferred embodiment, the mutant has a mutation at a position which is located no greater than 2.5 Å from a Type I copper site. In another preferred embodiment, the mutant has a mutation of an amino acid residue which is adjacent to a Type I copper site ligand. In another preferred embodiment, the mutant has a mutation of an amino acid residue which is a Type I copper site ligand.

The mutants of the present invention are mutants of a blue multi-copper oxidase. Preferably, the blue multi-copper oxidase is a bilirubin oxidase (Kokeida et al., 1993, *Journal of Biological Chemistry* 268: 18801–18809). In another preferred embodiment, the blue multi-copper oxidase is a phenoxazinone synthase (Freeman et al., 1993, *Biochemistry* 32: 4826–4830). In another preferred embodiment, the blue multi-copper oxidase is an ascorbate oxidase (Tauber et al., 1935, *Journal of Biological Chemistry* 110: 211). In another preferred embodiment, the blue multi-copper oxidase is a ceruloplasmin (Curzon and Young, 1972, *Biochimica Biophysica Acta* 268: 41). In another preferred embodiment, the blue multi-copper oxidase is a nitrite reductase (Godden et al., 1991, *Science* 253: 438–442). In another preferred embodiment, the blue multi-copper oxidase is a laccase. In a most preferred embodiment, the blue multi-copper oxidase is a fungal laccase, e.g., a Rhizoctonia laccase (preferably a *Rhizoctonia solani* laccase or RsL; WO 95/07988) or a Myceliophthora laccase (preferably a *Myceliophthora thermophilum* laccase or MtL described in U.S. application Ser. No. 08/253,781, which is incorporated herein by reference).

In another preferred embodiment, the oxidase is another Rhizoctonia laccase (as disclosed in U.S. application Ser. No. 08/172,331, which is incorporated herein by reference), another Myceliophthora laccase (as disclosed in U.S. application Ser. No. 08/253,781, which is incorporated herein by reference), and laccases of Polyporus (as disclosed in U.S. application Ser. No. 08/441,147, which is incorporated herein by reference), Trametes, Pyricularia, Coriolus, Scytalidium (as disclosed in U.S. application Ser. No. 08/253,784, which is incorporated herein by reference), Rigidoporus and Phenllinus (Geiger et al., 1986, *Appl. Biochem. Biotech.*, 13: 97–110), Podospora (Moltitoris and Reinhammar, 1974, *Biochimica Biophysica Acta* 386: 493–502), Lentinus (Leatham and Stahmann, 1980, *Journal of General Microbiology* 125: 147–157), Neurospora (Germann et al., 1987, *Journal of Biological Chemistry* 263: 885–896), Aspergillus (Kurtz and Champe, 1982, *Journal of Bacteriology* 151: 1338–1345), Phlebia (Niku-Paavola et al., 1988, *Biochemical Journal* 254:877–884), Botrytis (Dubernet et al., 1976, *Phytochemistry* 16: 191–193,), Sclerotia (Chet and Huttermann, 1982, *FEMS Microbiological Letters* 14: 211–215), Curvularia (Banerjee and Vohra, 1991, *Folia Microbiol.* 36: 343–346), Fomes (Haars and Huttermann, 1983, *Arch. Microbiol.* 134: 309–313), Schizophyllum (De Vries et al., 1986, *Journal of General Microbiology* 132: 2817–2826), Cerrena (Bekker et al., 1990, *Biokhimia* 55: 2019–2024), Armillaria (Rehman and Thurston, 1992, *Journal of General Microbiology* 138: 1251–1257), Agaricus (Perry et al., 1993, *Journal of General Microbiology* 139: 1209–1218), *Pleurotus* (Von Hunolstein et al., 1986, *Journal of General Applied Microbiology* 32: 185–191), Acer pseudopaltanus (Lafayette et al., 1995, *Plant Physiology* (Rockville) 107: 667–668), and *Rhus* (Bertrand, 1895, *C. R. Acad. Sci. Paris* 121: 166).

The mutants of the present invention may have a different specific activity than the wild-type blue copper oxidases. For example, a negative charge, or more precisely, a relatively high electron density, in the T1 copper site region is important for activity.

Furthermore, the mutants of the present invention may have a different pH-activity profile than the wild-type blue copper oxidases, e.g., the mutants can have a higher or lower pH optimum by an alteration of the charge distribution (or dielectric anisotrophy) at the T1 copper site. In order to enhance the activity of the oxidase of interest in a more alkaline pH range, electron density and/or negative charge should be increased. Thus, in the mutants of the present invention, (a) a neutral amino acid residue is substituted with a negative amino acid residue or (b) a positive amino acid residue is substituted with a negative or neutral amino acid residue. In addition, neutral residues equipped with a functional group that bear a relatively high electron density and could act as general base, such as histidine, serine, threonine, tyrosine, cysteine, and methionine, may also be used to substitute other neutral residues possessing only simple aliphatic or aromatic side chains, such as leucine and phenylalanine. In order to enhance the activity of the oxidase of interest in a more acidic pH range, electron density and/or negative charge should be decreased. Thus, in this embodiment of the mutants of the present invention, (a) a neutral amino acid residue is substituted with a positive amino acid residue or (b) a negative amino acid residue is substituted with a positive or neutral amino acid residue.

The present invention also relates to mutants which can be expressed in higher yields. Such mutants include oxidases comprising a substitution of a phenylalanine with another amino acid residue. For example, substituting phenylalanine at a position corresponding to residue 513 of *Myceliophthora thermophila* laccase and position 470 in *Rhizoctonia solani* isozyme 4 laccase results in a low expression yield. Thus, the mutants of the present invention encompass substitutions of Phe at one of these positions with another amino acid residue. Preferably, the amino acid residue does not ligate to copper, i.e., the amino acid residue is not histidine, cysteine, methionine, glutamate, and aspartate. Preferably, phenylalanine is substituted by leucine. In a preferred embodiment, the yield of the mutant enzyme is increased at least two-fold, more preferably at least five-fold, over the yield observed with the corresponding wild-type enzyme when both are expressed in the same host and fermented under the same conditions.

In a preferred embodiment, the mutants of the present invention comprise a mutation in a region corresponding to: (a) the segment that contains one Cu-ligating His, e.g., 416VIELNITGGADHPI429 (SEQ ID NO:25) of *Rhizoctonia solani* laccase and 421ENDPGAPFTLPHPM433 (SEQ ID NO:27) of *Myceliophthora thermophila* laccase; (b) the segment that contains another ligating His and the ligating Cys, e.g., 474GPWFVHCHIDWHLEAGLALVF494 (SEQ ID NO:25) of *Rhizoctonia solani* laccase and 497GAWLFHCHIAWHVSGGLGV515 (SEQ ID NO:27) of *Myceliophthora thermophila* laccase; (c) the segment corresponding to the sequence where Q353 and W362 of ascorbate oxidase reside, e.g., 356VSLNLAIGRSTVDGIL371 (SEQ ID NO:25) of *Rhizoctonia solani* laccase and 361VTLDTTGTPLFVWKVN376 (SEQ ID NO:27) of *Myceliophthora thermophila* laccase; (d) the segment corresponding to the sequence where R285 of ascorbate oxidase resides, e.g., 303LDPTNVFAVL312 (SEQ ID NO:25) of *Rhizoctonia solani* laccase and 308AIFHYAGAPG317 (SEQ ID NO:27) of *Myceliophthora thermophila* laccase; (e) the segment corresponding to the sequence where W163 of ascorbate oxidase resides, e.g., 217INVKRGKRYR226 (SEQ ID NO:25) of *Rhizoctonia solani* laccase and 222GRRHRLRLIN231 (SEQ ID NO:27) of *Myceliophthora thermophila* laccase; and (f) the segment corresponding to 465LEAGL472 (SEQ ID NO:25), more preferably 466LEAGL470 (SEQ ID NO:25), of *Rhizoctonia solani* laccase. Those skilled in the art will readily recognize, by routine homology alignment, the corresponding regions in other blue copper oxidases. In a preferred embodiment, the mutants comprise a mutation in the segment corresponding to 416VIELNITGGADHPI429 (SEQ ID NO:25) of *Rhizoctonia solani* laccase and 421ENDPGAPFTLPHPM433 (SEQ ID NO:27) of *Myceliophthora thermophila* laccase.

In a preferred embodiment, the mutants comprise at least two amino acid residues, more preferably at least 3 amino acid residues. In another preferred embodiment, the mutants comprise five mutations, more preferably four mutations, even more preferably three mutations, even more preferably two mutations, and most preferably one mutation.

The mutants described herein are most efficiently prepared by site-directed mutagenesis of the DNA encoding the wild-type laccase of interest. Such techniques are well-known in the art, and are described in, for example, Sambrook et al., 1989, *Molecular Cloning, A Laboratory Manual,* Cold Spring Harbor Laboratory, Cold Spring Harbor, N.Y. The present invention also encompasses the nucleic acid encoding the mutant laccases, as well as vectors and host cells comprising same, for use in recombinant expression of the mutant enzyme.

The choice of host cells and expression vectors will to a large extent depend upon the enzyme of choice and its source. The mutant gene can be expressed, in active form, using an expression vector. A useful expression vector contains an element that permits stable integration of the vector into the host cell genome or autonomous replication of the vector in a host cell independent of the genome of the host cell, and preferably one or more phenotypic markers which permit easy selection of transformed host cells. The expression vector may also include control sequences encoding a promoter, ribosome binding site, translation initiation signal, and, optionally, a repressor gene, a selectable marker or various activator genes. To permit the secretion of the expressed protein, nucleotides encoding a signal sequence may be inserted prior to the coding sequence of the gene. For expression under the direction of control sequences, a laccase gene to be used according to the invention is operably linked to the control sequences in the proper reading frame. Promoter sequences that can be incorporated into plasmid vectors, and which can direct the transcription of the laccase gene, include, but are not limited to, the prokaryotic β-lactamase promoter (Villa-Kamaroff et al., 1978, *Proceedings of the National Academy of Sciences USA* 75: 3727–3731) and the tac promoter (DeBoer et al., 1983, *Proceedings of the National Academy of Sciences USA* 80: 21–25). Further references can also be found in "Useful proteins from recombinant bacteria" in 1980, *Scientific American* 242: 74–94; and in Sambrook et al., 1989, supra.

The expression vector carrying the nucleic acid construct of the invention may be any vector which may be conveniently subjected to recombinant DNA procedures. The vector may be an autonomously replicating vector, i.e., a vector which exists as an extrachromosomal entity, the replication of which is independent of chromosomal replication, e.g., a plasmid, or an extrachromosomal element, minichromosome or an artificial chromosome. Alternatively, the vector may be one which, when introduced into a host cell, is integrated into the host cell genome and replicated together with the chromosome(s) into which it has been integrated.

In the vector, the nucleic acid sequence should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA construct of the invention, especially in a bacterial host, are the promoter of the lac operon of *E. coli*, the *Streptomyces coelicolor* agarase gene dagA promoters, the promoters of the *Bacillus licheniformis* alpha-amylase gene (amyL), the promoters of the *Bacillus stearothermophilus* maltogenic amylase gene (amyM), the promoters of the *Bacillus amyloliquefaciens* alpha-amylase (amyQ), or the promoters of the *Bacillus subtilis* xylA and xylB genes. In a yeast host, a useful promoter is the ENO-1 promoter. For transcription in a fungal host, examples of useful promoters are those derived from the gene encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase or *Aspergillus nidulans* acetamidase. Preferred are the TAKA-amylase and glaA promoters.

The expression vector of the invention may also comprise a suitable transcription terminator and, in eukaryotes, polyadenylation sequences operably connected to the DNA sequence encoding the laccase of the invention. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g., a gene the product of which complements a defect in the host cell, such as the dal genes from *Bacillus subtilis* or *Bacillus licheniformis*, or one which confers antibiotic resistance such as ampicillin, kanamycin, chloramphenicol or tetracycline resistance. Examples of Aspergillus selection markers include amdS, pyrG, argB, niaD, sC, and hygB a marker giving rise to hygromycin resistance. Preferred for use in an Aspergillus host cell are the amdS and pyrG markers of *Aspergillus nidulans* or *Aspergillus oryzae*. A frequently used mammalian marker is the dihydrofolate reductase (DHFR) gene. Furthermore, selection may be accomplished by co-transformation, e.g., as described in WO 91/17243.

It is generally preferred that expression gives rise to a product that is extracellular. The laccases of the present invention may thus comprise a preregion permitting secretion of the expressed protein into the culture medium. If desirable, this preregion may be native to the laccase of the invention or substituted with a different preregion or signal sequence, conveniently accomplished by substitution of the DNA sequences encoding the respective preregions. For example, the preregion may be derived from a glucoamylase or an amylase gene from an Aspergillus species, an amylase gene from a Bacillus species, a lipase or proteinase gene from *Rhizomucor miehei*, the gene for the alpha-factor from Saccharomyces cerevisiae, or the calf preprochymosin gene. Particularly preferred, when the host is a fungal cell, is the preregion for *Aspergillus oryzae* TAKA amylase, *Aspergillus niger* neutral amylase, the maltogenic amylase form Bacillus NCIB 11837, *Bacillus stearothermophilus* alpha-amylase, or Bacillus licheniformis subtilisin. An effective signal sequence is the *Aspergillus oryzae* TAKA amylase signal, the *Rhizomucor miehei* aspartic proteinase signal, and the *Rhizomucor miehei* lipase signal.

The procedures used to ligate the nucleic acid construct of the invention, the promoter, terminator and other elements, respectively, and to insert them into suitable vectors containing the information necessary for replication, are well known to persons skilled in the art (cf., for instance, Sambrook et al., 1989, supra).

The cell of the invention either comprising a nucleic acid construct or an expression vector of the invention as defined above is advantageously used as a host cell in the recombinant production of an enzyme of the invention. The cell may be transformed with the nucleic acid construct of the invention, conveniently by integrating the construct into the host chromosome. This integration is generally considered to be an advantage as the sequence is more likely to be stably maintained in the cell. Integration of the constructs into the host chromosome occurs by homologous or heterologous recombination. Alternatively, the cell may be transformed with an expression vector as described above in connection with the different types of host cells.

The host cell may be selected from prokaryotic cells, such as bacterial cells. Examples of suitable bacteria are gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis,* or *Streptomyces lividans* or *Streptomyces murinus,* or gram negative bacteria such as *E. coli.* The transformation of the bacteria may, for instance, be effected by protoplast transformation or by using competent cells in a manner known per se.

The host cell is preferably a eukaryote, such as mammalian cells, insect cells, plant cells or preferably fungal cells, including yeast and filamentous fungi. For example, useful mammalian cells include CHO or COS cells. A yeast host cell may be selected from a species of Saccharomyces or Schizosaccharomyces, e.g., *Saccharomyces cerevisiae.* Useful filamentous fungi may be selected from a species of Aspergillus, e.g., *Aspergillus oryzae* or *Aspergillus niger.* Alternatively, a strain of a Fusarium species, e.g., *Fusarium oxysporum,* or *Fusarium graminearum,* can be used as a host cell. Fungal cells may be transformed by a process involving protoplast formation and transformation of the protoplasts followed by regeneration of the cell wall in a manner known per se. A suitable procedure for transformation of Aspergillus host cells is described in EP 238 023. A suitable method of transforming Fusarium species is described by Malardier et al., 1989, *Gene* 78:147–156 or in copending U.S. application Ser. No. 08/269,449.

The present invention thus also provides a method of producing a recombinant protein of the invention, which method comprises cultivating a host cell as described above under conditions conducive to the production of the enzyme and recovering the enzyme from the cells and/or culture medium. The medium used to cultivate the cells may be any conventional medium suitable for growing the host cell in question and obtaining expression of the laccase of the invention. Suitable media are available from commercial suppliers or may be prepared according to published formulae (e.g., in catalogues of the American Type Culture Collection).

The resulting enzyme may be recovered from the medium by conventional procedures including separating the cells from the medium by centrifugation or filtration, precipitating the proteinaceous components of the supernatant or filtrate by means of a salt, e.g., ammonium sulphate, followed by purification by a variety of chromatographic procedures, e.g., ion exchange chromatography, gel filtration chromatography, affinity chromatography, or the like. Preferably, the isolated protein is about 90% pure as determined by SDS-PAGE, purity being most important in food, juice or detergent applications.

In a particularly preferred embodiment, the expression of the enzyme is achieved in a fungal host cell, such as Aspergillus. As described in detail in the following examples, the laccase gene is ligated into a plasmid containing the *Aspergillus oryzae* TAKA alpha-amylase promoter, and the *Aspergillus nidulans* amdS selectable marker. Alternatively, the amdS may be on a separate plasmid and used in co-transformation. The plasmid (or plasmids) is used to transform an Aspergillus species host cell, such as *Aspergillus oryzae* or *Aspergillus niger* in accordance with methods described in Yelton et al., 1984, *Proceedings of the National Academy of Sciences USA* 81: 1470–1474.

The modified oxidases, particularly laccases of the present invention can be used in a number of industrial methods. These processes include polymerization of lignin, both Kraft and lignosulfates, in solution, in order to produce a lignin with a higher molecular weight. Such methods are described in, for example, Jin et al., 1991, *Holzforschung* 45: 467–468; U.S. Pat. No. 4,432,921; EP 0 275 544; PCT/DK93/00217, 1992.

The oxidases of the present invention can also be used for in situ depolymerization of lignin in Kraft pulp, thereby producing a pulp with lower lignin content. This use of these enzymes is an improvement over the current use of chlorine for depolymerization of lignin, which leads to the production of chlorinated aromatic compounds, which are an environmentally undesirable by-product of paper mills. Such uses are described in, for example, *Current Opinion in Biotechnology* 3: 261–266, 1992; *Journal of Biotechnology* 25: 333–339, 1992; Hiroi et al., 1976, *Svensk Papperstidning* 5: 162–166.

Oxidation of dyes or dye precursors and other chromophoric compounds leads to decolorization of the compounds. Laccase can be used for this purpose, which can be particularly advantageous in a situation in which a dye transfer between fabrics is undesirable, e.g., in the textile industry and in the detergent industry. Methods for dye transfer inhibition and dye oxidation can be found in WO 92/01406, WO 92/18683, EP 0495836 and Calvo, 1991, *Mededelingen van de Faculteit Landbouw-wetenschappen/Rijiksuniversitet Gent.* 56: 1565–1567; Tsujino et al., 1991, *Journal of the Chemical Society* 42: 273–282; methods for the use of oxidation of dye and dye precursors in hair coloring are found in U.S. application Ser. No. 08/441,146 and 441,147, the contents of which are incorporated herein by reference.

The present laccase can also be used for the polymerization of phenolic or aniline compounds present in liquids. An example of such utility is the treatment of juices, such as apple juice, so that the laccase will accelerate a precipitation of the phenolic compounds present in the juice, thereby producing a more stable juice. Such applications have been described in Stutz, 1993, *Fruit Processing* 7/93, 248–252; Maier et al., 1990, *Dt. Lebensmittel-rindschau* 86: 137–142; Dietrich et al., 1990, *Fluss. Obst* 57: 67–73.

The present invention is further explained in the following non-limiting examples.

EXAMPLES

Materials and methods

Chemicals used as buffers and substrates are commercial products of at least reagent grade.

The protocols for molecular biology experiments (including restriction digests, DNA ligations, gel electrophoresis, and DNA preparations) are adapted from either the instructions of the manufacturer or standard procedures (Sambrook et al., 1989, supra). All oligonucleotides are synthesized by an Applied Biosystems 294 DNA/RNA Synthesizer. Nucleotide sequences are determined by an Applied Biosystems automatic DNA Sequencer, Model 373A, version 1.2.0.

Example

Site-directed mutagenesis of *Myceliophthora thermophila* laccase

The construction of a *Myceliophthora thermophila* laccase expression vector, pRaMB17, and several derivatives, pRaMB17M, pBANe22T, and pRaMB17Q, which direct expression of the *Myceliophthora thermophila* wild-type laccase and laccase variants, is shown FIGS. 1–4. The primers used in the constructions are summarized in Table 1.

TABLE 1

Primers

| Primer | Sequence |
|---|---|
| 1 | (forward) 5' dGTCGTCTACCTCGAGCGCGCC 3' (SEQ ID NO: 1) |
| 2 | (reverse) 5' dGTCATCTAGACGCTCACGCCTTGACCAGCCA 3' (SEQ ID NO: 2) |
| 3 | 5' dGTAGACGACGCCGAAGCCGCCCGAGAC 3' (SEQ ID NO: 3) |
| 4 | 5' dGACGACGCCCAGGCCAGCCTCGAGGTGCCAGGCGATGTG 3' (SEQ ID NO: 4) |
| 5 | 5' dGAGGTAGACGACGCCGAAGCCAGCCTCGAGGTGCCAGGCGATGTG 3' (SEQ ID NO: 5) |
| 6 | 5' CGGTACCGTCTAGAGTCGCGATGCATC 3' (SEQ ID NO: 6) |
| 7 | 3' CCGGGCCATGGCAGATCTCAGCGCTACGTAGGATC 5' (SEQ ID NO: 7) |
| 8 | 5' ATGATGAAGTCCTTCATCAGCGCCGCGACGCTTTTGGTGGG 3' (SEQ ID NO: 8) |
| 9 | 3' TACTACTTCAGGAAGTAGTCGCGGCGCTGCGAAAACCAC 5' (SEQ ID NO: 9) |
| 10 | (forward) 5' dGGGTCTAGAGGTGACTGACACCTGGCGGT 3' (SEQ ID NO: 10) |
| 11 | (reverse) 5' dTGACCCGGGAACTGGCCCCGACATTCCAGC 3' (SEQ ID NO: 11) |
| 12 | 5'-gggatttaaatATGAAGTCCTTCATCAGCGCC-3' (SEQ ID NO: 12) |
| 13 | 5'-gggttaattaaTtACGCCTTGACCAGCCACTCGCC-3' (SEQ ID NO: 13) |
| 14 | 5' ATACACAACTGGATGATGAAGTCCTTCATCAGCG 3' (SEQ ID NO: 14) |

Specifically, a small DNA fragment containing the 3'-terminus of the lcc-1 coding region (including stop codon) is generated by PCR using pRaMB5 (U.S. application Ser. No. 08/441,146, which is incorporated herein by reference) as a template for Pfu polymerase with primers 1 and 2 listed in Table 1. The 188 bp PCR product is digested with XbaI plus XhoI and purified by agarose gel electrophoresis. The purified fragment is then mixed in a three-part ligation reaction with an Asp718I-XhoI segment (1286 bp) of the lcc-1 gene from pRaMB5, and pUC518 (a derivative of pUC118; Vieira and Messing, 1987, *Methods in Enzymology* 153: 3–4), containing additional restriction sites for BglII, ClaI, XhoI and NsiI in the polylinker, which has been cleaved with Asp718I-XbaI. The resulting plasmid, pInt2.22, which contains approximately 1.5 kb of the lcc-1 coding region, is extended from an internal Asp718I site through the stop codon which is followed immediately by a XbaI site. Single-stranded pInt2.22 DNA template is prepared (Vieira and Messing, 1987, supra) and used as a template for oligonucleotide-directed mutagenesis (Adelman et al., 1983, *DNA* 2: 183–193) with primer 3 for L513F mutation, primer 4 for V509L/S510E/G511A mutation, and primer 5 for V509L/S510E/G511A/L513F mutation to derive the precursor plasmids for pRaMB17, pRaMB17M, pBANe22T and pRaMB17Q.

Mutants are identified by hybridization with radiolabeled oligonucleotide primers 3, 4, and 5, and each mutation is verified by DNA sequence analysis.

Figure 2:
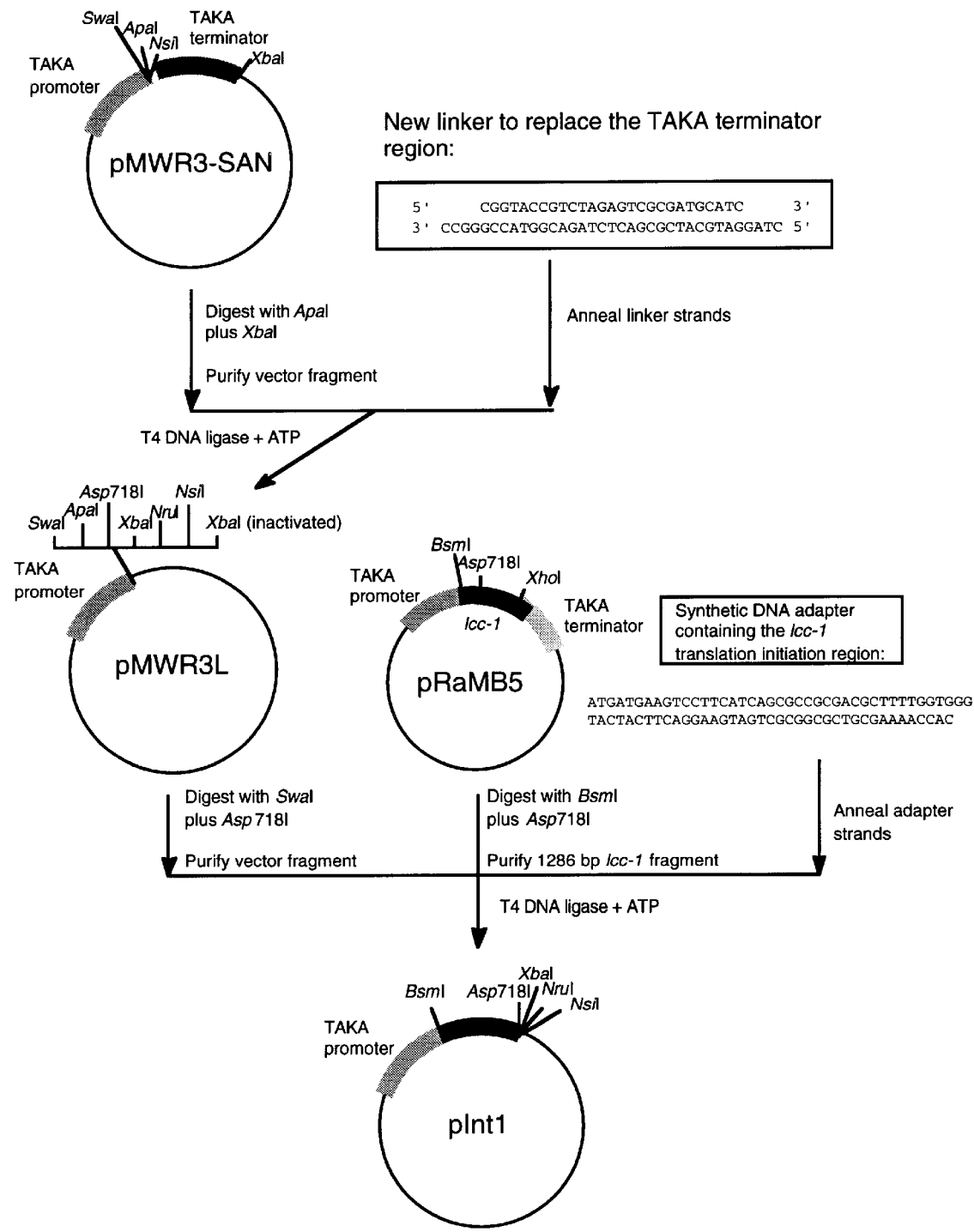
FIG. 2 shows the construction of the intermediate pInt1 which contains the Aspergillus oryzae TAKA amylase promoter and 5'-portion of the *Myceliophthora thermophila* lcc-1 coding region.
Figure 3:
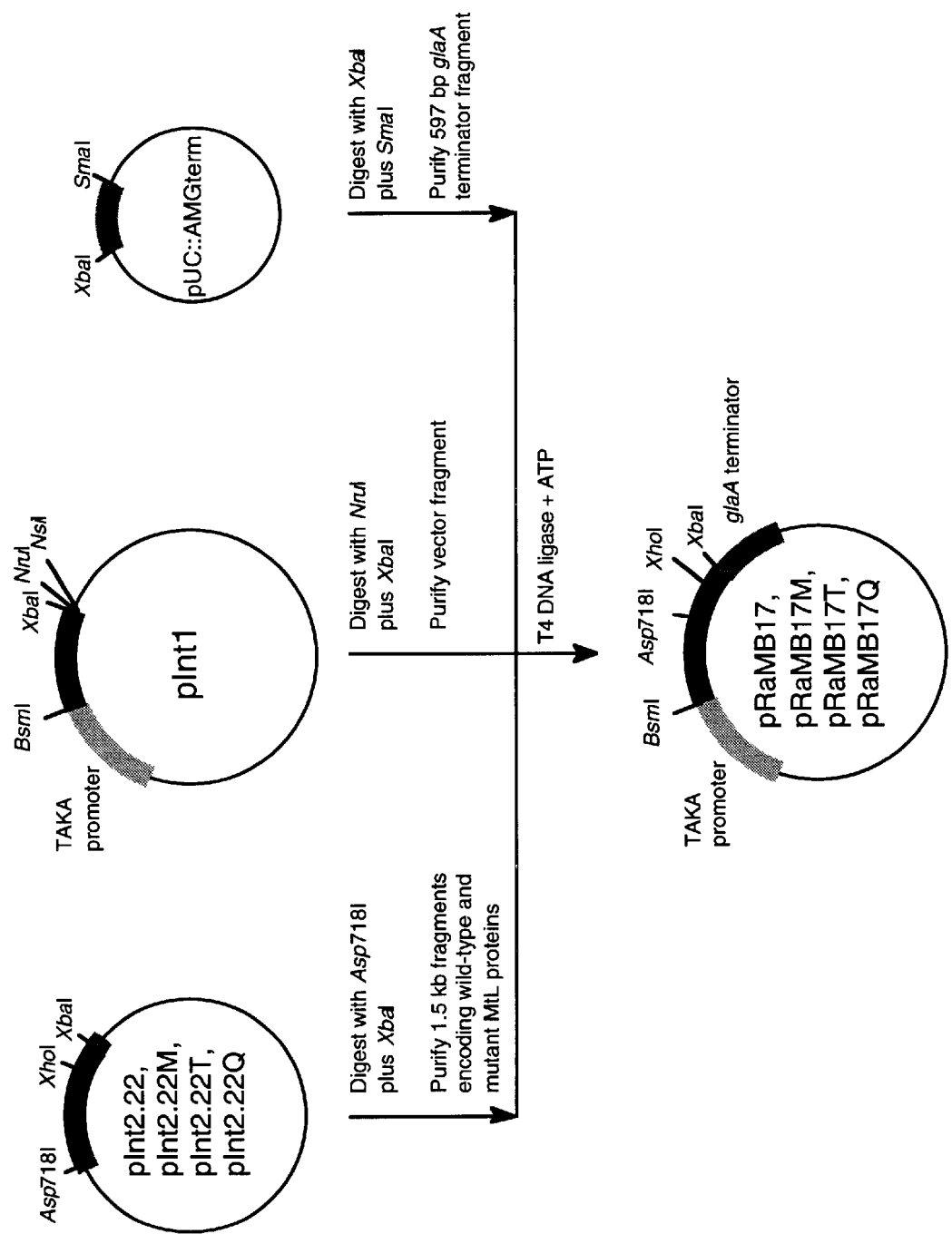
FIG. 3 shows the final step in construction of pRaMB17 and its derivatives, pRaMB17M and pRaMB17Q, which direct expression of wild-type and mutant forms of *Myceliophthora thermophila* laccase (MtL).

The next step in the construction of pRaMB17 and its derivatives is partially shown in FIG. 2. The starting plasmid, pMWR3-SAN, is prepared by cleaving bacteriophage vector M13mp18 (Yanisch-Perron et al., 1985, *Gene* 33: 103–119) with HindIII and EcoRI, and purifying the large vector fragment by agarose gel electrophoresis. This fragment is ligated with a synthetic DNA linker having the following sequence:

5'AATTCGTCGACGGYCTCTATTTCTGTACGGCCTTCA
GGTGGCCGCACCGGCCATGCATAG-
CAGCTGCCAGAGATAAAGACATGCCG-
GAAGTCCACCGGCGTGGCCGGTACGTATTCGA3' (SEQ ID NO:15)

The resulting phage vector, mp18-5' link, is then digested with SalI and BsaI (both sites in the synthetic linker region) and ligated with a 1.1 kb SalI-BsaI fragment from pTAKA-17 comprising the TAKA promoter region to generate the recombinant phage mp18-5'. Plasmid pUC18 (Yanisch-Perron etal., 1985, supra) is digested with HindIII plus EcoRI and the 2.6 kb vector fragment is purified by agarose gel electrophoresis. The isolated fragment is ligated with a synthetic linker with the following sequence:

5'AATTGTTTAAACTCTAGAGAAT-
TCAAGCTTGTCGACGTTTAAAC-
CAAATTTGAGATCTCTTAAGTTCGAA-
CAGCTGCAAATTTGTCGA3' (SEQ ID NO: 16)

The resulting plasmid, pUC18::TAKA-link, is digested with SalI plus EcoRI and the vector fragment is isolated by agarose gel electrophoresis. pTAKA-17 is used as a template for PCR amplification of a 0.7 kb TAKA-amylase terminator fragment. For this purpose, the following primers are used:

forward primer: 5'dATGCATAGGGTGGAGAGTATATGATGG3' (SEQ ID NO: 17)

reverse primer: 5'dCTGAATTCCGTTTCGTTTAC3' (SEQ ID NO: 18)

The 0.7 kb product of this PCR reaction is digested with NsiI plus EcoRI and mixed in a three-part ligation with SalI and EcoRI cleaved pUC18::TAKA-link and the 1.1 kb SalI-NsiI TAKA promoter fragment from mp18-5' to produce pMWR1.

Plasmid pMWRI is modified to generate pMWR3. First, a new TAKA-amylase promoter segment is generated by PCR using pTAKA-17 as a template with the following synthetic primers:

forward primer: 5'dTCCTGCAGAATGCAATTTAAACTC3' (SEQ ID NO: 19)

reverse primer: 5'dCTATGCATATTTAAATGCCTTCT-
GTGGGGTTTATTG3' (SEQ ID NO:20)

The 0.2 kb PCR product is digested with NsiI plus PstI and ligated with the large vector fragment of pMWR1 which has been cleaved with NsiI and PstI. The resulting plasmid, pMWR3, is then modified by inserting a small linker, AATTGGGCCCATGCA (SEQ ID NO:21), which contains an ApaI site between the SwaI and NsiI sites, creating pMWR3-SAN. A derivative of pMWR3-SAN is then constructed by replacing the ApaI-XbaI TAKA-amylase terminator fragment with a small linker (primers 6 and 7 shown in Table 1). This linker introduces Asp718I, XbaI, and NruI cloning sites and inactivates the XbaI site of pMWR3-SAN yielding pMWR3L.

pMWR3L is digested with SwaI and Asp718I and mixed in a three-part ligation with a 853 bp BsmI-Asp718I fragment comprising the 5'-end of the lcc-1 coding region and synthetic DNA adapter containing the translation initiation region (primers 8 and 9 shown in Table 1) to yield plasmid pInt1.

A 597 bp DNA segment comprising the *Aspergillus niger* glaA terminator region is then isolated by PCR using pHD414 (EP 238 023) as a template with primers 10 and 11 shown in Table 1, which introduce XbaI and SmaI sites at the 5' and 3'-ends of the terminator, respectively. The amplified DNA fragment is subsequently cleaved with XbaI plus SmaI and subcloned into pUC118 to generate plasmid pUC::AMGterm.

Finally, the 1.5 kb fragments containing the wild-type and mutant lcc-1 gene sequences are excised by digestion with Asp718I and XbaI and purified by agarose gel electrophoresis. Each of these fragments is mixed in a three part ligation (FIG. 3) with Asp718I and NruI digested pInt1 plus the 597 bp XbaI-SmaI glaA terminator fragment from pUC::AMGterm to produce pRaMB17, pRaMB17M, pRaMB17T and pRaMB17Q.

Figure 4:
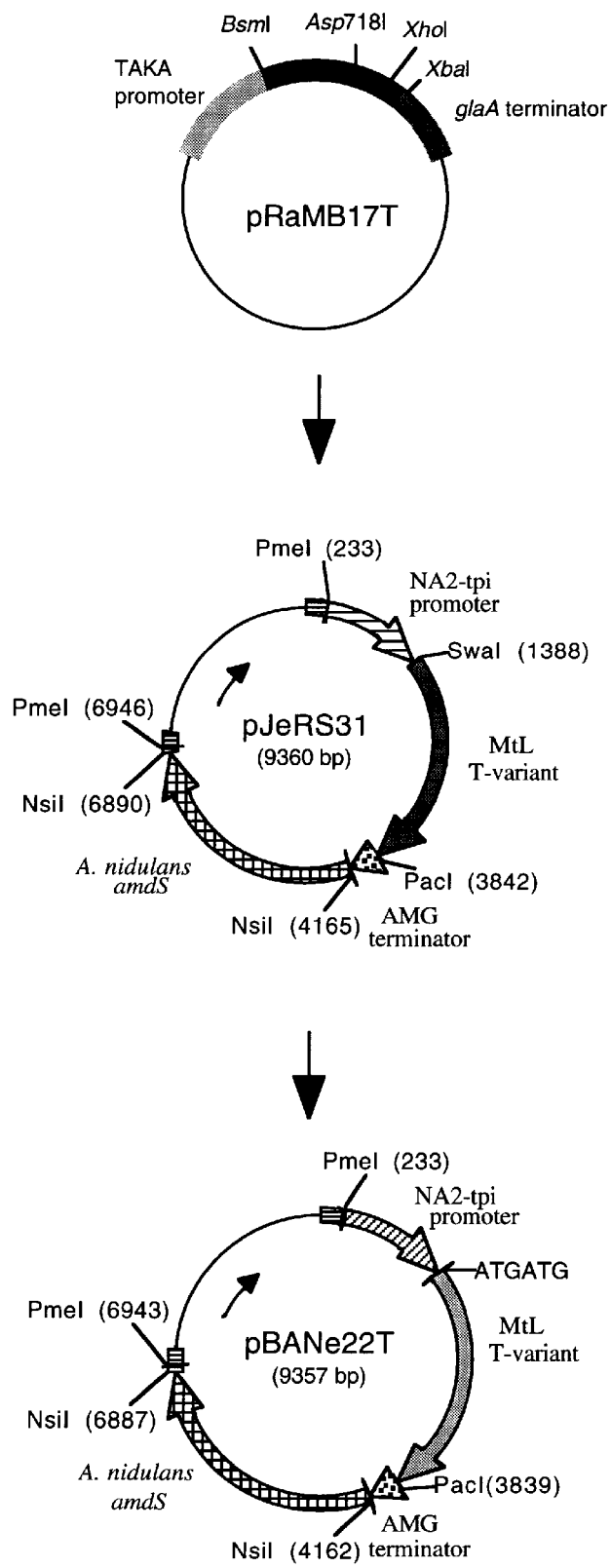
FIG. 4 shows the construction of pBANe22T which directs expression of a mutant form of *Myceliophthora thermophila* laccase.
Figure 5A:
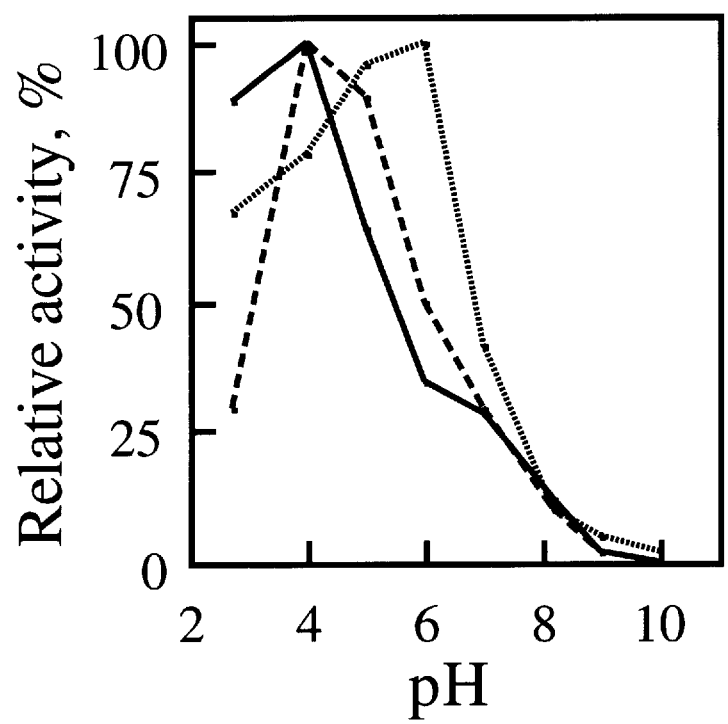
FIG. 5 shows the pH activity profiles of the wild-type (wt) and mutant *Rhizoctonia solani* laccases (RsLs) and *Myceliophthora thermophila* laccases (MtLs):wt(__); mutant M ( - - - ); mutant T ( . . . ); (A), RsL with 2,2'-azinobis(3-ethylbenzthiazoline-6-sulfonic acid) (ABTS); (B), RsLs with syringaldazine (SGZ); (C), MtLs with ABTS; (D), MtLS with SGZ.
Figure 5B:
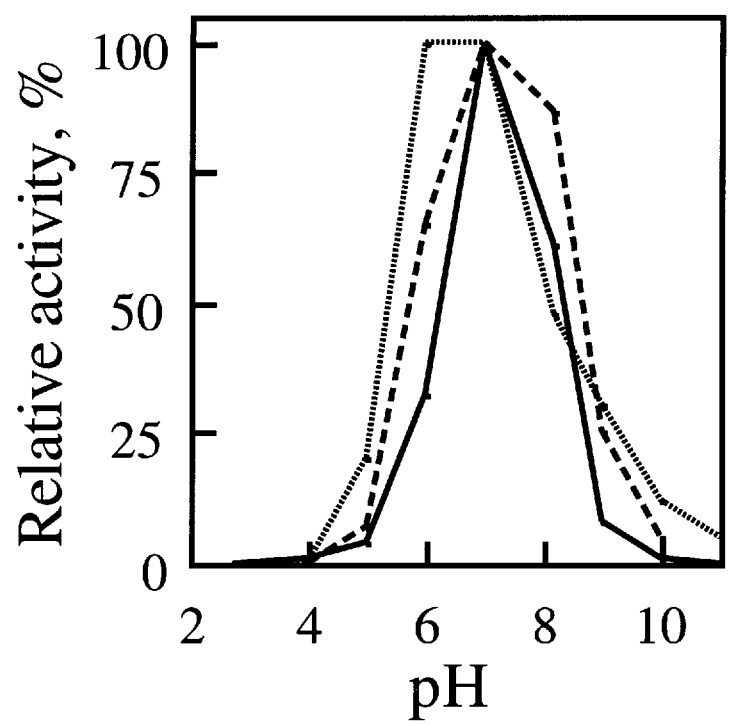
Figure 5C:
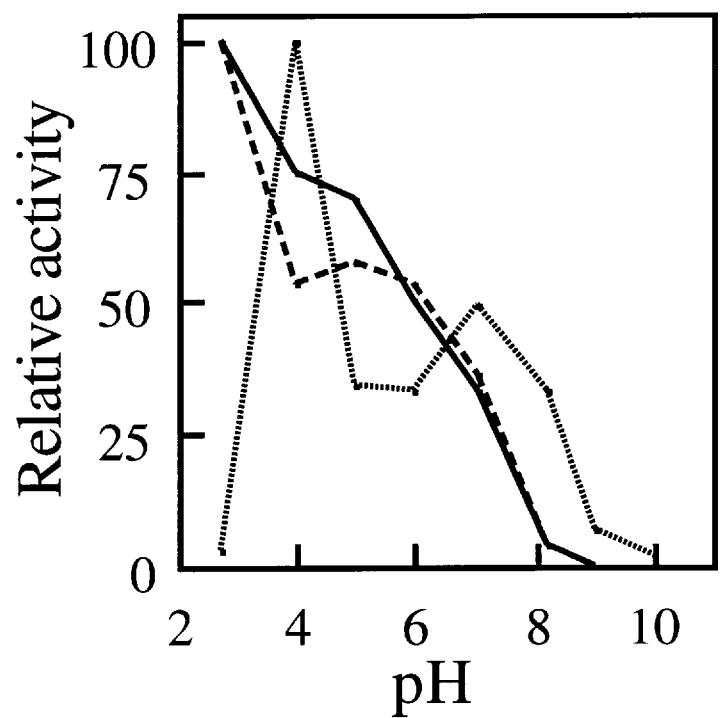
Figure 5D:
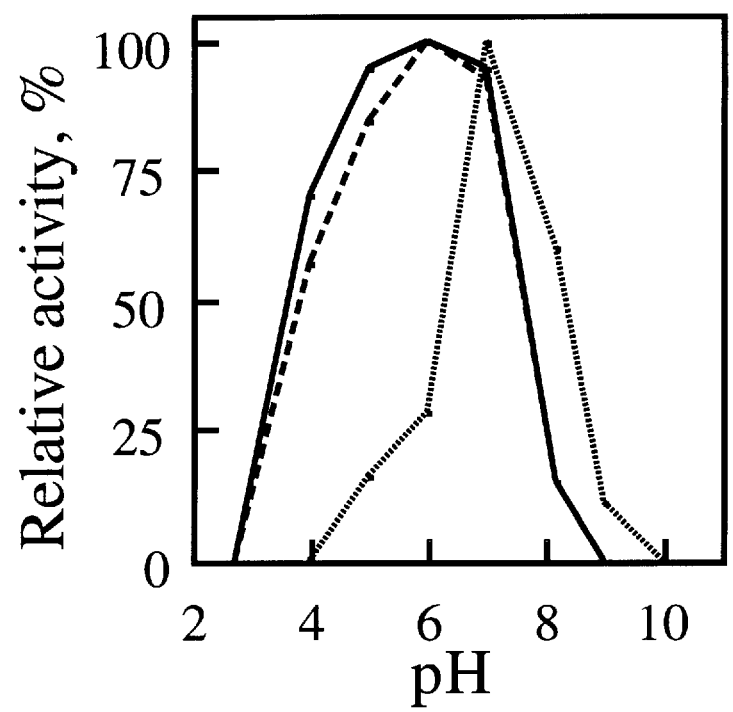

DNA primers 12 and 13 (uppercase letters represent sequences in the laccase gene) are used in a PCR reaction to amplify the mutant laccase gene from plasmid pRaMB17T (FIG. 4). The PCR is performed in a 50 ml reaction containing 120 ng of plasmid pRaMB17T, 0.05 mM each of dATP, dTTP, dGTP, dCTP, 100 pmol each of primers 12 and 13, 1X PwoI Buffer (Boehringer Mannheim, Indianapolis, Ind.), 5% (v/v) DMSO, and 2.5 units PwoI (Boeringer Mannheim, Indianapolis, Ind.). The PCR conditions are 95° C. for 3 minutes, 30 cycles each at 95° C. for 1 minute, 60° C. for 1 minute, and 72° C. for 1.5 minutes, and then 72° C. for 5 minutes. The PCR reaction mixture is run on a agarose gel and the 2.4 kb DNA laccase band is excised. The DNA is purified by solubilization of the agarose with 3 volumes Qia-ex solubilization buffer (Qiagen, Los Angeles, Calif.) followed by a Qiaquick PCR spin column according to the manufacturer's directions (Qiagen, Los Angeles, Calif.). The DNA is recovered in 50 ml of 1 mM EDTA-10 mM Tris pH 8 buffer. A 20 µl aliquot of the DNA is cut in a final volume of 25 µl containing 1X restriction enzyme buffers and restriction enzymes PacI and SwaI as suggested by the manufacturer. The reaction mixture is then heated at 80° C. for 10 minutes. One ml of the PacI/SwaI cut laccase gene is ligated into PacI/SwaI cut plasmid pBANe6. The ligation mixture is used to transform *E. coli* strain DH5α. The plasmid containing pBANe6 and the mutant laccase sequences is designated pJeRS31. pJeRS31 is subjected to site-directed mutagenesis using primer 14 to remove the SwaI site and add a second ATG using the MORPH Site-Specific Plasmid DNA Mutagenesis Kit according to the manufacturer's instructions (5 Prime 3 Prime, Inc., Boulder, Colo.) to produce pBANe22T.

A summary of the plasmids is provided in Table 2.

TABLE 2 pRaMB17 and its derivatives

| Vector | MtL protein encoded |
| --- | --- |
| pRaMB17 | Wild-type MtL |
| pRaMB17M | MtL with the L513F mutation |
| pBANe22T | MtL with the triple substitution V509L/S510E/G511A |
| pRaMB17Q | MtL with the quadruple substitution V509L/S510E/G511A/L513F |

Example 2

Transformation of *Aspergillus oryzae* with modified *Myceliophthora thermophila* laccase genes Methods for co-transformation of *Aspergillus oryzae* are described by Christensen et al., 1988, *Bio/Technology* 6: 1419–1422. For introduction of each of the *Myceliophthora thermophila* laccase expression vectors pRamB17, pRamB17M, pBANe22T, and pRamB17Q into *Aspergillus oryzae* HowB711, equal amounts (approximately 5 µg each) of the laccase expression vector and pToC90 (WO 91/17243) are added to approximately 106 protoplasts in suspension while pBANe22T is added alone. Transformants are selected on Cove medium (Cove, 1966, *Biochimica Biophysica Acta* 113: 51–56) containing 1M sucrose, 10 mM acetamide as the sole nitrogen source, and 20 mM CsCl to inhibit background growth. The transformants selected in this way are subsequently screened for the ability to produce laccase on Cove medium containing 1–3 mM ABTS. Cells which secrete active laccase oxidize the ABTS, producing a green halo surrounding the colony. Transformants which produce detectable laccase activity on ABTS plates are purified twice through conidiospores.

Example 3

Expression of modified *Myceliophthora thermophila* laccases

The transformants described in Example 2 are grown in shake flask cultures containing 25 ml of ASPO4 medium (pRaMB17, pRaMB17M, pRaMB17Q) or MY51 medium (pBANe22T) for 4 to 5 days at 37° C. ASPO4 medium is comprised of 1 g of $CaCl_2$-$2H_2O$, 2 g of yeast extract, 1 g of $MgSO_4$, 2 g of citric acid, 5 g of $KH_2PO_4$, 1 g of urea, 2 g of $(NH_4)_2SO_4$, 20 g of maltodextrin, and 0.5 ml of trace metals solution per liter. MY51 medium is comprised of 50 g of maltodextrin, 2 g $MgSO_4$-$7H_2O$, 10 g of $KH_2PO_4$, 2 g of citric acid, 10 g of yeast extract, 2 g of urea, 1 g of urea, 2 g of $(NH_4)_2SO_4$, and 0.5 ml of trace metals solution. The trace metals solution is comprised of 14.3 g of $ZnSO_4$-$7H_2O$, 2.5 g of $CuSO_4$-$5H_2O$, 0.5 g of $NiCl_2$-$6H_2O$, 13.8 g of $FeSO_4$-$7H_2O$, 8.5 g of $MgSO_4$-$H_2O$, and 3.0 g of citric acid per liter of RO water. Culture supernatants are assayed for laccase activity using either ABTS or syringaldazine as a substrate as described below.

Syringaldazine (SGZ) oxidation is determined in MES pH 5.3 buffer or Britten-Robinson buffer, pH 2.7 to 11.0, with 10% ethanol (coming from SGZ stock solution) by monitoring the absorbance change at 530 nm with an extinction coefficient of 65 $mM^{-1}cm^{-1}$ (Bauer and Rupe, 1971, *Analytical Chemistry* 43: 421–425) at 20° C. Laccase activity using SGZ as a substrate is assayed by mixing 800 µl of assay buffer (40 µM $CuSO_4$-25 mM sodium acetate pH 5.5) with 20 µl of culture supernatant and 60 µl of 0.28 mM syringaldazine in 50% ethanol. The absorbance at 530 nm is measured over time in a UV-VIS spectrophotometer. One laccase unit (LACU) is defined as the amount of enzyme which oxidizes one µmole of substrate per minute at 30° C.

ABTS oxidation is determined at pH 5 in a 96-well plate at 20° C. by monitoring the absorbance change at 405 nm with an extinction coefficient of 35 $mM^{-1}cm^{-1}$ (Childs and Bardsley, 1975, *Biochemical Journal* 145: 93–103). Laccase activity using ABTS as a substrate is measured by mixing 20 µl of culture supernatant with 200 µl of substrate solution containing 0.275 mg of ABTS per ml of 100 mM sodium acetate pH 5.0.

Shake flask cultures producing high levels of extracellular laccase activity are further evaluated by fermentation. A 1 ml aliquot of a spore suspension (approximately 109 spores) of an *Aspergillus oryzae* transformant expressing the laccase variant of interest is added aseptically to each of several 500 ml shake flasks containing 100 ml of medium comprised of 50 g of Nutriose 725, 2 g of MgSO$_4$-7H$_2$O, 10 g of KH$_2$PO$_4$, 2 g of K$_2$SO$_4$, 0.5 g of CaCl$_2$-2H$_2$O, 2 g of citric acid, 10 g of yeast extract, 0.5 ml of trace metals (as described above), and 2 g of urea per liter of tap water (adjusted to pH 6.0 before autoclaving) and incubated at 34° C. on a rotary shaker at 200 rpm for about 18 hours. Samples of the shake flask broths are then transferred to a laboratory fermentor containing medium, supplemented with 2 mM CuSO$_4$-5H$_2$O, comprised of 30 g of Nutriose, 5 g of yeast extract, 2 g of (NH$_4$)$_2$HPO$_4$, 2 g of MgSO$_4$-7H$_2$O, 4 g of citric acid, 3 g of K$_2$SO$_4$, 2 g of CaCl$_2$-H$_2$O, and 0.5 ml of trace metals solution (as described above) per liter and fed during the course of the fermentation with a medium comprised of 270 g of Nutriose, 30 g of urea, and 15 g of yeast extract per liter. The fermentaion is allowed to proceed at 31° C., pH 7, 600–700 rpm for 7 days.

1989, *Gene* 77: 51–59) together with the primers listed in Table 3. Primer 15 (SEQ ID NO:22) is used to create pJiWa85 that encodes three amino acid changes ("T": L466V/E467S/A468G) in the laccase coding region (Table 3). PCR amplification with primer 16 (SEQ ID NO:23) results in pJiWa86 which encodes a single amino acid mutation ("M": L470F). For each mutation, a 505 nt SacI/NorI fragment is generated by PCR and used to replace the homologous fragment in pJiWa59. PCR-amplified regions of the gene are sequenced to confirm the mutation as well as to ascertain the integrity of the coding region.

TABLE 3

Primers used for PCR mutagenesis of rsl4 gene.

| Primer 15 | C | ATT | GAC | TGG | CAC | GTG | TCG | GGT | GGG | CTC | GCA | CTT | G | |
| pJiWa85 | | I | D | W | H | V | S | G | G | L | A | L | | (SEQ ID NO: 28) |
| | | : | : | : | : | | | : | : | : | : | : | | |
| RSL-wt | H | I | D | W | H | L | E | A | G | L | A | L | V | (SEQ ID NO: 25) |
| rsl4 | CAC | ATT | GAC | TGG | CAC | TTG | GAG | GCT | GGG | CTC | GCA | CTT | GTC | (SEQ ID NO: 24) |
| | | : | : | : | : | : | : | : | : | | : | : | : | |
| pJiWa86 | | | | | | L | E | A | G | F | A | L | V | (SEQ ID NO: 29) |
| Primer 16 | | | | | C | TTG | GAG | GCT | GGG | TTC | GCA | CTT | GTC | |

Note. The amino acid translation of both the primers and the native gene are shown in italics. Homologous amino acids are noted by a colon between the two sequences. Those nucleotides in the PCR primers which differ from the gene sequence are underlined.

Laccase yields for the "M" (L513F) and "T" (V509L/S510E/G511A) mutants from these fermentations are estimated to be 25% and 40%, respectively, of the wild-type yield. In contrast, the expression yield of mutant "Q" (V509L/S510E/G511A/L513F) is so low that there is insufficient laccase for purification.

Example 4

Purification of modified *Myceliophthora thermophila* laccases

The wild-type, "M", and "T" fermentation broths from Example 3 are cheese-cloth filtered (pH 7.6, 16 mS), filtered through Whatman #2 filter paper, concentrated on a Spiral Concentrator (Amicon) with a S1Y100 membrane (100 kDa MW-CO), and diluted to 0.75 mS with glass distilled water. The washed concentrated broths are loaded onto a Q-Sepharose XK26 (Pharmacia, Uppsala, Sweden) column (120 ml), pre-equilibrated with 10 mM Tris, pH 7.5, 0.7 mS (Buffer A), and active fractions are eluted during the linear gradient with Buffer B (Buffer A plus 2M NaCl). The active fractions are pooled, adjusted to 1 mS in ionic strength, and subjected to a Mono-Q (Pharmacia, Uppsala, Sweden) chromatography equilibrated with Buffer A. Laccase preparations with apparent electrophoretic purity are obtained in the run-through fractions.

Example 5

Site-directed mutagenesis of *Rhizoctonia solani* laccase gene

Site-specific mutations are introduced into the *Rhizoctonia solani* laccase rsl4 gene of the expression plasmid, pJiWa59, using the overlap-extension PCR method (Ho, Example 6

Transformation of *Aspergillus* oryzae with the modified *Rhizoctonia solani* rsl4 genes

*Aspergillus oryzae* HowB711 is transformed with 8 µg of pJiWa85 ("T": L466V/E467S/A468G) or pJiWa86 ("M": L470F) together with 2 µg of pToC90 and *Aspergillus oryzae* HowB104 is transformed with 8 µg of pJiWa59 (wt) together with 2 µg of pToC90 using a standard PEG mediated protocol (Yelton, 1984, *Proceedings of the National Academy of Sciences* USA 81: 1470–1474). The transformants are selected on Minimal medium plates supplemented with 10 mM acetamide and 1M sucrose. The Minimal medium is comprised of 6.0 g of NaNO$_3$, 0.52 g of KCl, 1.52 g of KH$_2$PO$_4$, 1.0 ml of trace metals solution, 20 g of Nobel Agar (Difco), 20 ml of 50% glucose, 20 ml of methionine (50 g/l), 20 ml of biotin (200 mg/l), 2.5 ml of 20% MgSO$_4$-7H$_2$O, and 1.0 ml of mg/ml streptomycin per liter. The agar medium is adjusted to pH 6.5 prior to autoclaving and then glucose, methionine, biotin, MgSO$_4$-7H$_2$O, and streptomycin are added as sterile solutions to the cooled autoclaved medium and poured into plates. The trace metals solution is comprised of 0.04 g of Na$_2$B$_4$O$_7$-10H$_2$O, 0.4 g of CuSO$_4$-5H$_2$O, 1.2 g of FeSO$_4$-7H$_2$O, 0.7 g of MnSO$_4$-H$_2$O, 0.8 g of Na$_2$MoO$_2$-2H$_2$O, and 10 g of ZnSO$_4$-7H$_2$O per liter of RO water.

Laccase activity is scored on Minimal medium plates containing 10 mM acetamide and 1 g/l ABTS. Colonies that produce a green halo, indicative of laccase expression, are spore-purified twice.

Example 7

Expression of modified *Rhizoctonia solani* laccases

The spores from transformants of pJiWa59 (wt), pJiWa85 ("T"), and pJiWa86 ("M") described in Example 6 are used to inoculate 15 ml of MY51 medium in 125 ml shake flasks. After 3 days and 5 days growth at 37° C., a 1 ml aliquot is removed from each shake flask and centrifuged at 14,000 g for 5 minutes to remove any mycelia clumps. The supernatants are assayed for ABTS oxidation in 96-well microtiter plates as described below.

ABTS oxidation is determined in MES pH 5.3 buffer or Britten-Robinson buffer at pH 2.7 to 11.0 in a 96-well plate at 20° C. by monitoring the absorbance change at 405 nm with an extinction coefficient of 35 mM$^{-1}$cm$^{-1}$ (Childs and Bardsley, 1975, *Biochemical Journal* 145: 93–103).

The transformants yielding the highest laccase activity are selected for fermentation and grown as described in Example 3. Laccase yields for the "M" (L470F) and "T" (L466V/E467S/A468G) mutants from these fermentations are estimated to be 17% and 50%, respectively, of the wild-type yield.

Example 8

Purification of *Rhizoctonia solani* modified laccases

The wild-type, "M", and "T" fermentation broths from Example 7 are cheese-cloth filtered (pH 7.6, 16 mS), filtered through Whatman #2 filter paper, and concentrated on a Spiral Concentrator (Amicon) with a S1Y100 membrane (100 kDa MW-CO). The concentrated broths are then applied to a Q Sepharose column (XK26, 120 ml) (Pharmacia, Uppsala, Sweden), preequilibrated with 10 mM Tris pH 7.5, 0.7 mS (Buffer A). Active fractions run through the column during loading and washing. The active fractions are pooled, adjusted to pH 5.3 and applied on a SP-Sepharose column (XK16, 60 ml) (Pharmacia, Uppsala, Sweden), preequilibrated with 10 mM MES pH 5.3 buffer (Buffer C). The majority of activity is eluted by a linear gradient of Buffer D (Buffer C and 1 mM NaCl). The active fractions are adjusted to 20 mS and applied to a Sephadex 200 column (1610, 120 ml) (Pharmacia, Uppsala, Sweden), pre-equilibrated with Buffer E (Buffer C and 0.1M NaCl. Purified *Rhizoctonia solani* laccase fractions are eluted by Buffer E. A recovery of 1% or 5% and purification of 280- or 150-fold are achieved for mutants "M" and "T", respectively. The "T" mutant shows a three-fold higher yield than the "M" mutant, but two-fold lower yield than the wild-type laccase.

Example 9

Characterization of the modified *Myceliophthora thermophila* laccases and the *Rhizoctonia solani* modified laccases The Leu/Phe mutation causes a decrease in expression yield. RsL-"M" shows a yield which is three-fold lower than that of RsL-"T", and five-fold lower than that previously obtained for RsL-wild type; while MtL-"M" shows a yield approximately two-fold lower than that observed for MtL-"T" and five-fold lower than that observed for MtL-wild type. When *Polyporus pinsitus* laccase (PpL; U.S. application Ser. No. 08/441,147, which is incorporated herein by reference), *Rhizoctonia solani* laccase (including isozyme 1 and 3; WO 95/07988), MtL, *Scytalidium thermophilum* laccase (StL), and *Myrothecium verrucaria* bilirubin oxidase (BiO) are expressed in the same host (HowB104), the yields are in the order of BiO~MtL~StL>RsL-4 >RsL-1 ~PpL. Among these laccases, the residue corresponding to the modified Leu in the "M" mutants is: Phe for both PpL and RsL-1; Leu for RsL-4, MtL, and StL; and Met for BiO. It seems that a Phe at this particular position correlates to low expression yield of these laccases in *Aspergillus oryzae* HowB104 and HowB711 strains.

The triple mutations in RsL-mutant "T" (LEA→VSG), which eliminates the negative charge, decreases activity two orders of magnitude. The triple mutations in MtL-mutant "T" (VSG→LEA), which creates a negative charge, decreases activity 4-fold. In contrast, the "M" mutants, in which a Leu is replaced by a Phe, exhibit similar activity in comparison to their wild type counterparts. The *Rhizoctonia solani* results are consistent with the hypothesis which correlates the presence of negative charge(s) near the T1 Cu to the specific activity. The effect of the Glu in the selected pentapeptide segment could be attributed to general base-catalysis in which the negatively charged residue facilitates the electron transfer from the substrate to the T1 Cu by perturbing the substrate molecule and/or stabilizing the resulting electron-deficient intermediate or product molecule.

The molecular weights of the mature laccases are used to calculate both extinction coefficients and turnover numbers. The molecular weights are determined from the deduced amino acid sequences of the DNA sequences (FIG. 6: SEQ ID NOS:24 and 25, and FIG. 7: SEQ ID NOS:26 and 27). Protein concentrations (expressed as subunits) are measured based on the extinction coefficients determined by quantitative amino acid analysis.

Cyclic voltammetry measurements with a Pt electrode show a mid-potential of 0.76 V for Fe(dipyridyl)$_2$Cl$_3$ - Fe(dipyridyl)$_2$Cl$_2$ couple in 8 mM MES pH 5.3. The oxidation of ABTS and SGZ in 8 mM MES pH 5.3 yields a mid-potential of 0.70 and 0.63 V, respectively. The published redox potentials (E°) for the redox couples Fe(dipyridyl)$_2$Cl$_3$-Fe(dipyridyl)$_2$Cl$_2$, NaI$_3$- NaI, and K$_3$Fe (CN)6- K$_4$Fe(CN)$_6$ are 0.780, 0.536, and 0.433 V, respectively (Kolthoff and Tomsicek, 1936, *Journal of Physical Chemistry* 40: 247–255; O'Reilly, 1973, *Biochimica Biophysica Acta* 292: 509–515; Vanysek, 1992, In Lide, D. R., editor, *Handbook of Chemistry and Physics*, 73rd Edition, pages 8.17–8.22, CRC Press, Boca Raton, Fla.). The E° determination for *Rhizoctonia solani* laccase is performed in 8 mM MES pH 5.3 buffer with either 17 μM *Rhizoctonia solani* laccase, 0.2 mM Fe(bipyridyl)$_2$Cl$_2$, and 0.05–0.2 mM Fe(bipyridyl)$_2$Cl$_3$, or 71–78 μM *Rhizoctonia solani* laccase and 14–100 μM ABTS. The E° determination for MtL is performed in 8 mM MES, pH 5.3 with 0.14 mM MtL, 0.02–20 mM K$_3$Fe(CN)$_6$, and 2 mM K$_4$Fe(CN)$_6$; as well as with 31 μM MtL, 0.1 mM I$_2$, and 5–19 mM NaI. Britten-Robinson buffer is used for other pHs.

Under various potentials of the solution poised by various concentration ratios of the redox couples, the absorbance changes of laccase in the range of 550–800 nm are monitored and the concentrations of the oxidized copper (II) and reduced copper (I) states are calculated after the spectral change reaches equilibrium. The concentrations of the redox couples at equilibrium are calculated from the initial concentrations and the concentration changes caused by the interaction with laccase. In the case of measuring E° of *Rhizoctonia solani* laccase with ABTS, the concentration of ABTS cation radical (ABTS+) is measured by the absorption at 810 nm (where *Rhizoctonia solani* laccase has no contribution) and then the spectral contribution of ABTS+ at 600 nm is subtracted from the observed absorption value in order to assess the spectral change of *Rhizoctonia solani* laccase. Anaerobicity is achieved by repetitive evacuating and argon-flushing the reaction chamber at 4° C.

The mutants exhibit similar chromatographic elution patterns to their wild type counterparts. The purified preparations have a characteristic blue color typical of a laccase and show other typical laccase properties as shown in Table 4. All the mutants can be retained by a 100 kDa MW-CO membrane, indicating a dimeric nature.

TABLE 4

Properties of *Myceliophthora thermophila* and *Rhizoctonia solani* laccase mutants

| | MW*, kDa | λmax (ε)† | E° at pH 5.3‡ |
|---|---|---|---|
| pJiWa59 (wt) | 70–85 | 276 (66), 330 sh (4.6), 602 (4.7) | 0.73 ± 0.02 |
| pJiWa86 ("M") | 70–90 | 276 (63), 330 sh (2.6), 600 (3.7) | 0.72 ± 0.02 |
| pJiWa85 ("T") | 70–90 | 276 (63), 330 sh (1.7), 600 (4.8) | 0.74 ± 0.03 |
| pRaMB17 (wt) | 75–90 | 276 (134), 330 sh (8.4), 589 (4.2) | 0.47 ± 0.01 |
| pRaMB17M ("M") | 70–90 | 280 (134), 330 sh (6.1), 600 (3.8) | 0.50 ± 0.01 |
| pBANe22T ("T") | 70–90 | 276 (134), 330 sh (4.2), 600 (2.9) | ND¤ |

*Estimated on SDS-PAGE.
†Units: 1 max, nm; e, $mM^{-1}cm^{-1}$. Calculated extinction coefficients are used.
‡in V vs NHE.
¤Not determined.

$K_m$ and $k_{cat}$ are obtained from the initial rate (v), enzyme concentration (E), and substrate concentration (S) in accordance to the equation $v=k_{cat}ES/(K_m+S)$ by non-linear regression fitting using the Prizm program (GraphPad, San Diego, Calif.). The $K_m$ and $k_{cat}$ for ABTS and SGZ are measured spectroscopically in 8 mM MES-NaOH buffer, pH 5.3; while the values for other substrates are measured by oxygen electrode in Britten-Robinson buffer, pH 5.1 with a Hansatech DW1/AD device (Norfolk, England), with 0.4–4 μlaccase in 0.3–0.5 ml Britten-Robinson buffer. The $O_2$ concentration in air-saturated buffer solution is assumed as the same in plain water (0.28 mM).

Tables 5 and 6 summarize the SGZ and ABTS oxidase activities of the mutants. For both *Rhizoctonia solani* laccase and *Myceliophthora thermophila* laccase, more profound difference is observed on the mutant "T" than that on the mutant "M" in comparison with the wild type. FIG. 5 shows the pH-activity profiles of the mutants with ABTS and SGZ. For ABTS oxidation, a significant change is seen with RsL-"T", MtL-"M", and MtL-"T". The optimal pH of RsL-"T" is shifted ≧1 unit in comparison with the wild type laccase. For SGZ oxidation, an optimal pH at 7 is observed for MtL-"T", in contrast to the range of 5–7 for the wild type laccase. In terms of pH profile, the elimination of the negative charge in RsL-"T" induces a shift of the optimal pH in the acidic direction for SGZ oxidation, probably due to the reduced acidity at the T1 site caused by the Glu removal. The creation of a negative charge in MtL-"T" induces a shift of the optimal pH for activity on the alkaline direction, which could be attributed to the increased acidity at MtL's T1 site caused by the creation of the negative charge.

TABLE 5

Syringaldazine oxidase activity of the mutants

| | LACU* | SOU† | ($pH_{opt}$) |
|---|---|---|---|
| RsL wt | 4.3 | 11 | (7) |
| RsL "M" | 2.2 | 4.7 | (6) |
| RsL "T" | 0.024 | 0.048 | (7) |
| MtL wt | 42 | 35 | (6) |
| MtL "M" | 24 | 25 | (6) |
| MtL "T" | 2 | 10 | (7) |

Activity unit: $\mu mol\ min^{-1}\ mg^{-1}$.
*25 mM sodium acetate pH 5.5, 30° C..
†B&R buffer, 20° C., at optimal pH (value in parenthesis).

TABLE 6

Syringaldazine and ABTS oxidase activity of the mutants

| | SGZ | | ABTS | |
|---|---|---|---|---|
| | $K_m, \mu M$ | $k_{cat}, min^{-1}$ | $K_m, \mu M$ | $k_{cat}, min^{-1}$ |
| RsL wt | 28 ± 4 | 550 ± 40 | 52 ± 6 | 2500 ± 100 |
| RsL "M" | 35 ± 4 | 255 ± 11 | 125 ± 13 | 760 ± 30 |
| RsL "T" | 3.9 ± 0.3 | 1.1 ± 0.1 | 60 ± 4 | 20 ± 1 |
| MtL wt | 1.4 ± 0.2 | 4500 ± 200 | 110 ± 20 | 3800 ± 300 |
| MtL "M" | 1.8 ± 0.2 | 3300 ± 100 | 43 ± 3 | 1800 ± 100 |
| MtL: "T" | 0.9 ± 0.2 | 360 ± 20 | 11 ± 2 | 530 ± 20 |

---

What is claimed is:

1. A mutant of a Myceliophthora laccase which comprises a substitution of one or more amino acid residues in one or more regions which correspond to the regions 222GRRHRLRLIN231 (SEQ ID NO:27), 308AIFHYAGAPG317 (SEQ ID NO:27), 361VTLDTTGTPLFVWKVN376 (SEQ ID NO:27), 421ENDPGAPFTLPHPM433 (SEQ ID NO:27), and 497GAWLFHCHIAWHVSGGLGV515 (SEQ ID NO:27) of the amino acid sequence of the Myceliophthora thermophila laccase of SEQ ID NO:27 and the mutant has laccase activity.

2. The mutant of claim 1, which is a mutant of a Myceliophthora thermophila laccase.

3. The mutant of claim 2, wherein the Myceliophthora thermophila laccase has an amino acid sequence of SEQ ID NO:27.

4. The mutant of claim 1 which comprises a substitution of one or more amino acid residues in the region 222GRRHRLRLIN231 (SEQ ID NO:27) of Myceliophthora thermophila laccase.

5. The mutant of claim 1 which comprises a substitution of one or more amino acid residues in the region 308AIFHYAGAPG317 (SEQ ID NO:27) of Myceliophthora thermophila laccase.

6. The mutant of claim 1 which comprises a substitution of one or more amino acid residues in the region 361VTLDTTGTPLFVWKVN376 (SEQ ID NO:27) of Myceliophthora thermophila laccase.

7. The mutant of claim 1 which comprises a substitution of one or more amino acid residues in the region 421 ENDPGAPFTLPHPM433 (SEQ ID NO: 27) of Myceliophthora thermophila laccase.

8. The mutant of claim 1 which comprises a substitution of one or more amino acid residues in the region 497GAWLFHCHIAWHVSGGLGV515 (SEQ ID NO:27) of Myceliophthora thermophila laccase.

9. The mutant of claim 1 in which (a) a neutral amino acid residue is substituted with a negative amino acid residue or (b) a positive amino acid residue is substituted with a negative or neutral amino acid residue.

10. The mutant of claim 1 in which a phenylalanine is substituted with another amino acid residue.

11. The mutant of claim 10 in which the other amino acid residue is a leucine.

12. The mutant of claim 1 in which (a) a neutral amino acid residue is substituted with a positive amino acid residue or (b) a negative amino acid residue is substituted with a positive or neutral amino acid residue.

13. The mutant of claim 1 in which leucine or phenylalanine is substituted with a neutral residue selected from the group consisting of histidine, serine, threonine, tyrosine, cysteine, and methionine.

14. The mutant of claim 1 which is modified by at least two amino acid residues.

15. The mutant of claim 1 which is modified by at least three amino acid residues.

16. The mutant of claim 1 which comprises the substitution L513F.

17. The mutant of claim 1 which comprises the substitutions V509L/S510E/G511A.

18. The mutant of claim 1 which comprises the substitutions V509L/S510E/G511A/L513F.

* * * * *

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 21 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:1:

GTCGTCTACC TCGAGCGCGC C 21

(2) INFORMATION FOR SEQ ID NO:2:

(i) SEQUENCE CHARACTERISTICS:
(A) LENGTH: 31 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

GTCATCTAGA CGCTCACGCC TTGACCAGCC A 31

(2) INFORMATION FOR SEQ ID NO:3:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

GTAGACGACG CCGAAGCCGC CCGAGAC 27

(2) INFORMATION FOR SEQ ID NO:4:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

GACGACGCCC AGGCCAGCCT CGAGGTGCCA GGCGATGTG 39

(2) INFORMATION FOR SEQ ID NO:5:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

GAGGTAGACG ACGCCGAAGC CAGCCTCGAG GTGCCAGGCG ATGTG 45

(2) INFORMATION FOR SEQ ID NO:6:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: cDNA ( x i ) SEQUENCE DESCRIPTION: SEQ ID NO:6:

CGGTACCGTC TAGAGTCGCG ATGCATC 27

( 2 ) INFORMATION FOR SEQ ID NO:7:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:7:

CCGGGCCATG GCAGATCTCA GCGCTACGTA GGATC 35

( 2 ) INFORMATION FOR SEQ ID NO:8:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:8:

ATGATGAAGT CCTTCATCAG CGCCGCGACG CTTTTGGTGG G 41

( 2 ) INFORMATION FOR SEQ ID NO:9:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

TACTACTTCA GGAAGTAGTC GCGGCGCTGC GAAAACCAC 39

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

GGGTCTAGAG GTGACTGACA CCTGGCGGT 29

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:11:

TGACCCGGGA ACTGGCCCCG ACATTCCAGC 30

( 2 ) INFORMATION FOR SEQ ID NO:12:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

```
GGGATTTAAA TATGAAGTCC TTCATCAGCG CC                                32
```

( 2 ) INFORMATION FOR SEQ ID NO:13:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:13:

```
GGGTTAATTA ATTACGCCTT GACCAGCCAC TCGCC                             35
```

( 2 ) INFORMATION FOR SEQ ID NO:14:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

```
ATACACAACT GGATGATGAA GTCCTTCATC AGCG                              34
```

( 2 ) INFORMATION FOR SEQ ID NO:15:

( i ) SEQUENCE CHARACTERISTICS:
        ( A ) LENGTH: 117 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

```
AATTCGTCGA CGGCTCTATT TCTGTACGGC CTTCAGGTGG CCGCACCGGC CATGCATAGC   60
AGCTGCCAGA GATAAAGACA TGCCGGAAGT CCACCGGCGT GGCCGGTACG TATTCGA     117
```

( 2 ) INFORMATION FOR SEQ ID NO:16:

( i ) SEQUENCE CHARACTERISTICS:
        ( A ) LENGTH: 88 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:16:

```
AATTGTTTAA ACTCTAGAGA ATTCAAGCTT GTCGACGTTT AAACCAAATT TGAGATCTCT   60
TAAGTTCGAA CAGCTGCAAA TTTGTCGA                                     88
```

( 2 ) INFORMATION FOR SEQ ID NO:17:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:17:

ATGCATAGGG TGGAGAGTAT ATGATGG      27

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:18:

CTGAATTCCG TTTCGTTTAC      20

( 2 ) INFORMATION FOR SEQ ID NO:19:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

TCCTGCAGAA TGCAATTTAA ACTC      24

( 2 ) INFORMATION FOR SEQ ID NO:20:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

CTATGCATAT TTAAATGCCT TCTGTGGGGT TTATTG      36

( 2 ) INFORMATION FOR SEQ ID NO:21:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:21:

AATTGGGCCC ATGCA      15

( 2 ) INFORMATION FOR SEQ ID NO:22:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:22:

CACATTGACT GGCACTTGGA GGCTGGGCTC GCACTTGTC 39

( 2 ) INFORMATION FOR SEQ ID NO:23:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:23:

CTTGGAGGCT GGGTTCGCAC TTGTC 25

( 2 ) INFORMATION FOR SEQ ID NO:24:

( i ) SEQUENCE CHARACTERISTICS:
        ( A ) LENGTH: 1588 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1587

( x i ) SEQUENCE DESCRIPTION: SEQ ID NO:24:

```
ATG CTT TCT AGC ATT ACC CTC CTA CCT TTG CTC GCT GCG GTC TCA ACC      48
Met Leu Ser Ser Ile Thr Leu Leu Pro Leu Leu Ala Ala Val Ser Thr
 1               5                  10                  15

CCC GCC TTT GCT GCC GTC CGC AAC TAT AAG TTC GAC ATC AAG AAC GTC      96
Pro Ala Phe Ala Ala Val Arg Asn Tyr Lys Phe Asp Ile Lys Asn Val
            20                  25                  30

AAT GTC GCT CCC GAT GGC TTT CAG CGC TCT ATC GTC TCC GTC AAC GGT     144
Asn Val Ala Pro Asp Gly Phe Gln Arg Ser Ile Val Ser Val Asn Gly
        35                  40                  45

TTA GTT CCT GGC ACG TTG ATC ACG GCC AAC AAG GGT GAC ACC TTG CGC     192
Leu Val Pro Gly Thr Leu Ile Thr Ala Asn Lys Gly Asp Thr Leu Arg
    50                  55                  60

ATT AAT GTC ACG AAT CAA CTC ACG GAC CCT AGT ATG CGT CGT GCC ACA     240
Ile Asn Val Thr Asn Gln Leu Thr Asp Pro Ser Met Arg Arg Ala Thr
65                  70                  75                  80

ACG ATT CAT TGG CAT GGA TTG TTC CAA GCT ACT ACC GCC GAC GAG GAT     288
Thr Ile His Trp His Gly Leu Phe Gln Ala Thr Thr Ala Asp Glu Asp
                85                  90                  95

GGC CCC GCA TTC GTC ACG CAA TGC CCT ATT GCG CAA AAT TTG TCC TAT     336
Gly Pro Ala Phe Val Thr Gln Cys Pro Ile Ala Gln Asn Leu Ser Tyr
            100                 105                 110

ACA TAC GAG ATC CCA TTG CGC GGC CAA ACA GGA ACC ATG TGG TAT CAC     384
Thr Tyr Glu Ile Pro Leu Arg Gly Gln Thr Gly Thr Met Trp Tyr His
        115                 120                 125

GCC CAT CTT GCG AGT CAA TAT GTC GAT GGA TTG CGA GGC CCT TTG GTC     432
Ala His Leu Ala Ser Gln Tyr Val Asp Gly Leu Arg Gly Pro Leu Val
    130                 135                 140

ATC TAT GAT CCA AAC GAC CCA CAC AAG TCG CGC TAC GAC GTG GAT GAT     480
Ile Tyr Asp Pro Asn Asp Pro His Lys Ser Arg Tyr Asp Val Asp Asp
145                 150                 155                 160

GCG AGC ACA GTA GTC ATG CTT GAG GAC TGG TAC CAT ACT CCG GCA CCC     528
```

|  |  |  |  |  |  |  |  |  |  |  |  |  |  |  |  |  |
|---|---|---|---|---|---|---|---|---|---|---|---|---|---|---|---|---|
| Ala | Ser | Thr | Val | Val<br>165 | Met | Leu | Glu | Asp<br>170 | Trp | Tyr | His | Thr | Pro<br>175 | Ala | Pro | |
| GTT | CTA | GAA | AAG | CAA | ATG | TTC | TCG | ACT | AAT | AAC | ACC | GCT | CTG | CTC | TCT | 576 |
| Val | Leu | Glu | Lys<br>180 | Gln | Met | Phe | Ser | Thr<br>185 | Asn | Asn | Thr | Ala | Leu<br>190 | Leu | Ser | |
| CCT | GTT | CCG | GAC | TCG | GGT | CTT | ATC | AAT | GGC | AAA | GGG | CGC | TAT | GTG | GGC | 624 |
| Pro | Val | Pro<br>195 | Asp | Ser | Gly | Leu | Ile<br>200 | Asn | Gly | Lys | Gly | Arg<br>205 | Tyr | Val | Gly | |
| GGT | CCC | GCA | GTT | CCC | CGG | TCA | GTA | ATC | AAC | GTA | AAA | CGT | GGG | AAA | CGA | 672 |
| Gly | Pro<br>210 | Ala | Val | Pro | Arg | Ser<br>215 | Val | Ile | Asn | Val | Lys<br>220 | Arg | Gly | Lys | Arg | |
| TAT | CGC | TTG | CGC | GTA | ATC | AAC | GCT | TCT | GCT | ATC | GGG | TCG | TTT | ACC | TTT | 720 |
| Tyr<br>225 | Arg | Leu | Arg | Val | Ile<br>230 | Asn | Ala | Ser | Ala | Ile<br>235 | Gly | Ser | Phe | Thr | Phe<br>240 | |
| TCG | ATC | GAA | GGA | CAT | AGT | CTG | ACT | GTC | ATT | GAG | GCC | GAT | GGG | ATC | CTG | 768 |
| Ser | Ile | Glu | Gly | His<br>245 | Ser | Leu | Thr | Val | Ile<br>250 | Glu | Ala | Asp | Gly | Ile<br>255 | Leu | |
| CAC | CAG | CCC | TTG | GCT | GTT | GAC | AGC | TTC | CAG | ATT | TAC | GCT | GGA | CAA | CGC | 816 |
| His | Gln | Pro | Leu<br>260 | Ala | Val | Asp | Ser | Phe<br>265 | Gln | Ile | Tyr | Ala | Gly<br>270 | Gln | Arg | |
| TAC | TCT | GTC | ATC | GTT | GAA | GCC | AAC | CAA | ACC | GCC | GCC | AAC | TAC | TGG | ATT | 864 |
| Tyr | Ser | Val<br>275 | Ile | Val | Glu | Ala | Asn | Gln<br>280 | Thr | Ala | Ala | Asn | Tyr<br>285 | Trp | Ile | |
| CGT | GCA | CCA | ATG | ACC | GTT | GCA | GGA | GCC | GGA | ACC | AAT | GCA | AAC | TTG | GAC | 912 |
| Arg | Ala<br>290 | Pro | Met | Thr | Val | Ala<br>295 | Gly | Ala | Gly | Thr | Asn<br>300 | Ala | Asn | Leu | Asp | |
| CCC | ACC | AAT | GTC | TTT | GCC | GTA | TTG | CAC | TAC | GAG | GGA | GCG | CCC | AAC | GCC | 960 |
| Pro<br>305 | Thr | Asn | Val | Phe | Ala<br>310 | Val | Leu | His | Tyr | Glu<br>315 | Gly | Ala | Pro | Asn | Ala<br>320 | |
| GAA | CCC | ACG | ACG | GAA | CAA | GGC | AGT | GCT | ATC | GGT | ACT | GCA | CTC | GTT | GAA | 1008 |
| Glu | Pro | Thr | Thr | Glu<br>325 | Gln | Gly | Ser | Ala | Ile<br>330 | Gly | Thr | Ala | Leu | Val<br>335 | Glu | |
| GAG | AAC | CTC | CAT | GCG | CTC | ATC | AAC | CCT | GGC | GCT | CCG | GGC | GGC | TCC | GCT | 1056 |
| Glu | Asn | Leu | His<br>340 | Ala | Leu | Ile | Asn | Pro<br>345 | Gly | Ala | Pro | Gly | Gly<br>350 | Ser | Ala | |
| CCC | GCA | GAC | GTT | TCC | CTC | AAT | CTT | GCA | ATT | GGG | CGC | AGC | ACA | GTT | GAT | 1104 |
| Pro | Ala | Asp<br>355 | Val | Ser | Leu | Asn | Leu<br>360 | Ala | Ile | Gly | Arg | Ser<br>365 | Thr | Val | Asp | |
| GGG | ATT | CTT | AGG | TTC | ACA | TTT | AAT | AAC | ATC | AAG | TAC | GAG | GCT | CCT | TCG | 1152 |
| Gly | Ile | Leu<br>370 | Arg | Phe | Thr | Phe | Asn<br>375 | Asn | Ile | Lys | Tyr | Glu<br>380 | Ala | Pro | Ser | |
| TTG | CCC | ACG | CTC | TTG | AAG | ATT | TTG | GCA | AAC | AAT | GCG | AGC | AAT | GAC | GCC | 1200 |
| Leu<br>385 | Pro | Thr | Leu | Leu | Lys<br>390 | Ile | Leu | Ala | Asn | Asn<br>395 | Ala | Ser | Asn | Asp | Ala<br>400 | |
| GAT | TTC | ACG | CCA | AAT | GAG | CAC | ACT | ATC | GTA | TTG | CCA | CAC | AAT | AAA | GTT | 1248 |
| Asp | Phe | Thr | Pro | Asn<br>405 | Glu | His | Thr | Ile | Val<br>410 | Leu | Pro | His | Asn | Lys<br>415 | Val | |
| ATC | GAG | CTC | AAT | ATC | ACC | GGA | GGT | GCA | GAC | CAC | CCT | ATC | CAT | CTC | CAC | 1296 |
| Ile | Glu | Leu | Asn<br>420 | Ile | Thr | Gly | Gly | Ala<br>425 | Asp | His | Pro | Ile | His<br>430 | Leu | His | |
| GGC | CAT | GTG | TTT | GAT | ATC | GTC | AAA | TCA | CTC | GGT | GGT | ACC | CCG | AAC | TAT | 1344 |
| Gly | His | Val<br>435 | Phe | Asp | Ile | Val | Lys<br>440 | Ser | Leu | Gly | Gly | Thr<br>445 | Pro | Asn | Tyr | |
| GTC | AAC | CCG | CCA | CGC | AGG | GAC | GTA | GTT | CGT | GTC | GGA | GGC | ACC | GGT | GTG | 1392 |
| Val | Asn | Pro<br>450 | Pro | Arg | Arg | Asp | Val<br>455 | Val | Arg | Val | Gly | Gly<br>460 | Thr | Gly | Val | |
| GTA | CTC | CGA | TTC | AAG | ACC | GAT | AAC | CCA | GGC | CCA | TGG | TTT | GTT | CAC | TGC | 1440 |
| Val<br>465 | Leu | Arg | Phe | Lys | Thr<br>470 | Asp | Asn | Pro | Gly | Pro<br>475 | Trp | Phe | Val | His | Cys<br>480 | |
| CAC | ATT | GAC | TGG | CAC | TTG | GAG | GCT | GGG | CTC | GCA | CTT | GTC | TTT | GCC | GAG | 1488 |

|  |  |  |  |  |  |  |  |  |  |  |  |  |  |  |  |
|---|---|---|---|---|---|---|---|---|---|---|---|---|---|---|---|
| His | Ile | Asp | Trp | His<br>485 | Leu | Glu | Ala | Gly | Leu<br>490 | Ala | Leu | Val | Phe | Ala<br>495 | Glu |
| GCC | CCC | AGC | CAG | ATT | CGC | CAG | GGT | GTC | CAG | TCG | GTC | CAG | CCC | AAC | AAT |
| Ala | Pro | Ser<br>500 | Gln | Ile | Arg | Gln | Gly | Val<br>505 | Gln | Ser | Val | Gln<br>510 | Pro | Asn | Asn |
| GCC | TGG | AAC | CAG | CTC | TGC | CCC | AAG | TAC | GCG | GCT | CTT | CCT | CCC | GAT | TTG |
| Ala | Trp | Asn<br>515 | Gln | Leu | Cys | Pro | Lys<br>520 | Tyr | Ala | Ala | Leu | Pro<br>525 | Pro | Asp | Leu |
| CAG | T |  |  |  |  |  |  |  |  |  |  |  |  |  |  |
| Gln |  |  |  |  |  |  |  |  |  |  |  |  |  |  |  |

1536

1584

1588

( 2 ) INFORMATION FOR SEQ ID NO:25:

( i ) SEQUENCE CHARACTERISTICS:
  ( A ) LENGTH: 529 amino acids
  ( B ) TYPE: amino acid
  ( D ) TOPOLOGY: linear ( i i ) MOLECULE TYPE: protein ( x i ) SEQUENCE DESCRIPTION: SEQ ID NO:25:

| Met<br>1 | Leu | Ser | Ser | Ile<br>5 | Thr | Leu | Leu | Pro | Leu<br>10 | Leu | Ala | Ala | Val | Ser<br>15 | Thr |
|---|---|---|---|---|---|---|---|---|---|---|---|---|---|---|---|
| Pro | Ala | Phe | Ala<br>20 | Ala | Val | Arg | Asn | Tyr<br>25 | Lys | Phe | Asp | Ile | Lys<br>30 | Asn | Val |
| Asn | Val | Ala<br>35 | Pro | Asp | Gly | Phe | Gln<br>40 | Arg | Ser | Ile | Val | Ser<br>45 | Val | Asn | Gly |
| Leu | Val<br>50 | Pro | Gly | Thr | Leu | Ile<br>55 | Thr | Ala | Asn | Lys | Gly<br>60 | Asp | Thr | Leu | Arg |
| Ile<br>65 | Asn | Val | Thr | Asn | Gln<br>70 | Leu | Thr | Asp | Pro | Ser<br>75 | Met | Arg | Arg | Ala | Thr<br>80 |
| Thr | Ile | His | Trp | His<br>85 | Gly | Leu | Phe | Gln | Ala<br>90 | Thr | Thr | Ala | Asp | Glu<br>95 | Asp |
| Gly | Pro | Ala | Phe<br>100 | Val | Thr | Gln | Cys | Pro<br>105 | Ile | Ala | Gln | Asn | Leu<br>110 | Ser | Tyr |
| Thr | Tyr | Glu<br>115 | Ile | Pro | Leu | Arg | Gly<br>120 | Gln | Thr | Gly | Thr | Met<br>125 | Trp | Tyr | His |
| Ala | His<br>130 | Leu | Ala | Ser | Gln | Tyr<br>135 | Val | Asp | Gly | Leu | Arg<br>140 | Gly | Pro | Leu | Val |
| Ile<br>145 | Tyr | Asp | Pro | Asn | Asp<br>150 | Pro | His | Lys | Ser | Arg<br>155 | Tyr | Asp | Val | Asp | Asp<br>160 |
| Ala | Ser | Thr | Val | Val<br>165 | Met | Leu | Glu | Asp | Trp<br>170 | Tyr | His | Thr | Pro | Ala<br>175 | Pro |
| Val | Leu | Glu | Lys<br>180 | Gln | Met | Phe | Ser | Thr<br>185 | Asn | Asn | Thr | Ala | Leu<br>190 | Leu | Ser |
| Pro | Val | Pro<br>195 | Asp | Ser | Gly | Leu | Ile<br>200 | Asn | Gly | Lys | Gly | Arg<br>205 | Tyr | Val | Gly |
| Gly | Pro<br>210 | Ala | Val | Pro | Arg | Ser<br>215 | Val | Ile | Asn | Val | Lys<br>220 | Arg | Gly | Lys | Arg |
| Tyr<br>225 | Arg | Leu | Arg | Val | Ile<br>230 | Asn | Ala | Ser | Ala | Ile<br>235 | Gly | Ser | Phe | Thr | Phe<br>240 |
| Ser | Ile | Glu | Gly | His<br>245 | Ser | Leu | Thr | Val | Ile<br>250 | Glu | Ala | Asp | Gly | Ile<br>255 | Leu |
| His | Gln | Pro | Leu<br>260 | Ala | Val | Asp | Ser | Phe<br>265 | Gln | Ile | Tyr | Ala | Gly<br>270 | Gln | Arg |
| Tyr | Ser | Val<br>275 | Ile | Val | Glu | Ala | Asn<br>280 | Gln | Thr | Ala | Ala | Asn<br>285 | Tyr | Trp | Ile |

| | | | | | | | | | | | | | | |
|---|---|---|---|---|---|---|---|---|---|---|---|---|---|---|
| Arg | Ala | Pro | Met | Thr | Val | Ala | Gly | Ala | Gly | Thr | Asn | Ala | Asn | Leu | Asp |
| | 290 | | | | | 295 | | | | | 300 | | | | |
| Pro | Thr | Asn | Val | Phe | Ala | Val | Leu | His | Tyr | Glu | Gly | Ala | Pro | Asn | Ala |
| 305 | | | | | 310 | | | | | 315 | | | | | 320 |
| Glu | Pro | Thr | Thr | Glu | Gln | Gly | Ser | Ala | Ile | Gly | Thr | Ala | Leu | Val | Glu |
| | | | | 325 | | | | | 330 | | | | | 335 | |
| Glu | Asn | Leu | His | Ala | Leu | Ile | Asn | Pro | Gly | Ala | Pro | Gly | Gly | Ser | Ala |
| | | | 340 | | | | | 345 | | | | | 350 | | |
| Pro | Ala | Asp | Val | Ser | Leu | Asn | Leu | Ala | Ile | Gly | Arg | Ser | Thr | Val | Asp |
| | | 355 | | | | | 360 | | | | | 365 | | | |
| Gly | Ile | Leu | Arg | Phe | Thr | Phe | Asn | Asn | Ile | Lys | Tyr | Glu | Ala | Pro | Ser |
| | 370 | | | | | 375 | | | | | 380 | | | | |
| Leu | Pro | Thr | Leu | Leu | Lys | Ile | Leu | Ala | Asn | Asn | Ala | Ser | Asn | Asp | Ala |
| 385 | | | | | 390 | | | | | 395 | | | | | 400 |
| Asp | Phe | Thr | Pro | Asn | Glu | His | Thr | Ile | Val | Leu | Pro | His | Asn | Lys | Val |
| | | | | 405 | | | | | 410 | | | | | 415 | |
| Ile | Glu | Leu | Asn | Ile | Thr | Gly | Gly | Ala | Asp | His | Pro | Ile | His | Leu | His |
| | | | 420 | | | | | 425 | | | | | 430 | | |
| Gly | His | Val | Phe | Asp | Ile | Val | Lys | Ser | Leu | Gly | Gly | Thr | Pro | Asn | Tyr |
| | | 435 | | | | | 440 | | | | | 445 | | | |
| Val | Asn | Pro | Pro | Arg | Arg | Asp | Val | Val | Arg | Val | Gly | Gly | Thr | Gly | Val |
| | 450 | | | | | 455 | | | | | 460 | | | | |
| Val | Leu | Arg | Phe | Lys | Thr | Asp | Asn | Pro | Gly | Pro | Trp | Phe | Val | His | Cys |
| 465 | | | | | 470 | | | | | 475 | | | | | 480 |
| His | Ile | Asp | Trp | His | Leu | Glu | Ala | Gly | Leu | Ala | Leu | Val | Phe | Ala | Glu |
| | | | | 485 | | | | | 490 | | | | | 495 | |
| Ala | Pro | Ser | Gln | Ile | Arg | Gln | Gly | Val | Gln | Ser | Val | Gln | Pro | Asn | Asn |
| | | | 500 | | | | | 505 | | | | | 510 | | |
| Ala | Trp | Asn | Gln | Leu | Cys | Pro | Lys | Tyr | Ala | Ala | Leu | Pro | Pro | Asp | Leu |
| | | 515 | | | | | 520 | | | | | 525 | | | |
| Gln | | | | | | | | | | | | | | | |

(2) INFORMATION FOR SEQ ID NO:26:

(i) SEQUENCE CHARACTERISTICS:
  (A) LENGTH: 3192 base pairs
  (B) TYPE: nucleic acid
  (C) STRANDEDNESS: single
  (D) TOPOLOGY: linear (ii) MOLECULE TYPE: DNA (genomic)

(ix) FEATURE:
  (A) NAME/KEY: CDS
  (B) LOCATION: join(587..832, 918..995, 1080..1091, 1194..1265,
   1338..2309, 2457..2525, 2619..3029)

(xi) SEQUENCE DESCRIPTION: SEQ ID NO:26:

```
GCTAGCTTCT TTGGTCACCG TCGTTTTCGC CCGCCCCCTC CCTCCTTCAA CCCCCTGAGT      60
AGTCGGCTAA GCGATCCTCA ATCTGGTCTT GTGAGGTCAC GTCCTCCAGC AGATGACAGT     120
TCATCGAGCG AGTGATCTCC ACCACCCAGA AGGGAGGGGG GATGCGCGCA TGCTCCAACA     180
TACCCTGGTG TCGCTAGAGA CGTCGCGGCA TCAGCCTTTT CATCACACCG AGCACGTCCA     240
CGGACCGGCT CCTTTCACCC CCGCGTCCTC CGGAGGATTG AGTCACGATA TTTCGGGATG     300
TGGGAAGGGG GAGAGAAAGG AGGGGGGAGG GGCGGAAACA TGTTGGATAC GAGCTGCGCC     360
CCTTTTCCAA CATCGAGAAC AGGAAGTCGT TGGTGTCGGC CGTAATGTCT ATAAAACGAG     420
GCTCCTTCTC GTCGTCGACT TGTCTCAGGT TCTCTCTCTC GTCCACACCA AGCCAGTCTT     480
```

```
GCCTGAGCCA CCTGAGCCAC CTTCAACTCA TCATCTTCAG TCAAGTCGTT CATTGACATT      540

GTGTCTCTCT TTCTATCGAG TCGGCTTCCC GGCCCTTCAC CACAAC ATG AAG TCC         595
                                                    Met Lys Ser
                                                     1

TTC ATC AGC GCC GCG ACG CTT TTG GTG GGC ATT CTC ACC CCT AGC GTT        643
Phe Ile Ser Ala Ala Thr Leu Leu Val Gly Ile Leu Thr Pro Ser Val
         5                  10                  15

GCT GCT GCC CCT CCA TCC ACC CCT GAG CAG CGC GAC CTG CTC GTC CCG        691
Ala Ala Ala Pro Pro Ser Thr Pro Glu Gln Arg Asp Leu Leu Val Pro
 20                  25                  30                  35

ATC ACG GAG AGG GAG GAG GCA GCC GTG AAG GCT CGC CAG CAG AGC TGC        739
Ile Thr Glu Arg Glu Glu Ala Ala Val Lys Ala Arg Gln Gln Ser Cys
             40                  45                  50

AAC ACC CCC AGC AAC CGG GCG TGC TGG ACT GAC GGA TAC GAC ATC AAC        787
Asn Thr Pro Ser Asn Arg Ala Cys Trp Thr Asp Gly Tyr Asp Ile Asn
                 55                  60                  65

ACC GAC TAC GAA GTG GAC AGC CCG GAC ACG GGT GTT GTT CGG CCG            832
Thr Asp Tyr Glu Val Asp Ser Pro Asp Thr Gly Val Val Arg Pro
         70                  75                  80

GTGAGTGCTC TCGTTAATTA CGCTTCGGCG AGTTGCGCAG ATATATTAAA TACTGCAAAC      892

CTAAGCAGGA GCTGACATGC GACAG TAC ACT CTG ACT CTC ACC GAA GTC GAC        944
                              Tyr Thr Leu Thr Leu Thr Glu Val Asp
                                      85                  90

AAC TGG ACC GGA CCT GAT GGC GTC GTC AAG GAG AAG GTC ATG CTG GTT        992
Asn Trp Thr Gly Pro Asp Gly Val Val Lys Glu Lys Val Met Leu Val
                 95                  100                 105

AAC GTACGGCACC CCTTTTCTTG TCCTAGGATC TGGGTGATGT GCGTCGTTGC            1045
Asn

CCCTGAGAGA GACTGACCGA GCCTTTGGCT GCAG AAT AGT ATA ATC GTAATTAATT     1101
                                      Asn Ser Ile Ile
                                          110

ATACCGCCCT GCCTCCAGCA GCCCCAGCAG CTCGAGAAGG GTATCTGAAG TTAGTCAGGC     1161

CTGCTGACCT GACCGGGGCC AACCCACCAT AG GGA CCA ACA ATC TTT GCG GAC       1214
                                     Gly Pro Thr Ile Phe Ala Asp
                                                 115

TGG GGC GAC ACG ATC CAG GTA ACG GTC ATC AAC AAC CTC GAG ACC AAC       1262
Trp Gly Asp Thr Ile Gln Val Thr Val Ile Asn Asn Leu Glu Thr Asn
120                 125                 130                 135

GGC GTATGTCTGC TGCTTGCTCT CTTGCTCTCC TCGTCCGCGA CTAATAATAA            1315
Gly

TATCAACTCG TGTGGAAAAC AG ACG TCG ATC CAC TGG CAC GGA CTG CAC CAG      1367
                         Thr Ser Ile His Trp His Gly Leu His Gln
                                         140                 145

AAG GGC ACC AAC CTG CAC GAC GGC GCC AAC GGT ATC ACC GAG TGC CCG       1415
Lys Gly Thr Asn Leu His Asp Gly Ala Asn Gly Ile Thr Glu Cys Pro
            150                 155                 160

ATC CCC CCC AAG GGA GGG AGG AAG GTG TAC CGG TTC AAG GCT CAG CAG       1463
Ile Pro Pro Lys Gly Gly Arg Lys Val Tyr Arg Phe Lys Ala Gln Gln
                165                 170                 175

TAC GGG ACG AGC TGG TAC CAC TCG CAC TTC TCG GCC CAG TAC GGC AAC       1511
Tyr Gly Thr Ser Trp Tyr His Ser His Phe Ser Ala Gln Tyr Gly Asn
        180                 185                 190

GGC GTG GTC GGG GCC ATT CAG ATC AAC GGA CCG GCC TCG CTG CCG TAC       1559
Gly Val Val Gly Ala Ile Gln Ile Asn Gly Pro Ala Ser Leu Pro Tyr
195                 200                 205                 210

GAC ACC GAC CTG GGT GTG TTC CCC ATC AGC GAC TAC TAC TAC AGC TCG       1607
Asp Thr Asp Leu Gly Val Phe Pro Ile Ser Asp Tyr Tyr Tyr Ser Ser
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 215 |     |     |     |     | 220 |     |     |     |     | 225 |     |      |
| GCC | GAC | GAG | CTG | GTG | GAA | CTC | ACC | AAG | AAC | TCG | GGC | GCG | CCC | TTC | AGC | 1655 |
| Ala | Asp | Glu | Leu | Val | Glu | Leu | Thr | Lys | Asn | Ser | Gly | Ala | Pro | Phe | Ser |      |
|     |     |     | 230 |     |     |     |     | 235 |     |     |     |     | 240 |     |     |      |
| GAC | AAC | GTC | CTG | TTC | AAC | GGC | ACG | GCC | AAG | CAC | CCG | GAG | ACG | GGC | GAG | 1703 |
| Asp | Asn | Val | Leu | Phe | Asn | Gly | Thr | Ala | Lys | His | Pro | Glu | Thr | Gly | Glu |      |
|     |     | 245 |     |     |     |     | 250 |     |     |     |     | 255 |     |     |     |      |
| GGC | GAG | TAC | GCC | AAC | GTG | ACG | CTC | ACC | CCG | GGC | CGG | CGG | CAC | CGC | CTG | 1751 |
| Gly | Glu | Tyr | Ala | Asn | Val | Thr | Leu | Thr | Pro | Gly | Arg | Arg | His | Arg | Leu |      |
|     | 260 |     |     |     |     | 265 |     |     |     |     | 270 |     |     |     |     |      |
| CGC | CTG | ATC | AAC | ACG | TCG | GTC | GAG | AAC | CAC | TTC | CAG | GTC | TCG | CTC | GTC | 1799 |
| Arg | Leu | Ile | Asn | Thr | Ser | Val | Glu | Asn | His | Phe | Gln | Val | Ser | Leu | Val |      |
| 275 |     |     |     |     | 280 |     |     |     |     | 285 |     |     |     |     | 290 |      |
| AAC | CAC | ACC | ATG | TGC | ATC | ATC | GCC | GCC | GAC | ATG | GTG | CCC | GTC | AAC | GCC | 1847 |
| Asn | His | Thr | Met | Cys | Ile | Ile | Ala | Ala | Asp | Met | Val | Pro | Val | Asn | Ala |      |
|     |     |     |     | 295 |     |     |     |     | 300 |     |     |     |     | 305 |     |      |
| ATG | ACG | GTC | GAC | AGC | CTC | TTC | CTC | GGC | GTC | GGC | CAG | CGT | TAC | GAT | GTC | 1895 |
| Met | Thr | Val | Asp | Ser | Leu | Phe | Leu | Gly | Val | Gly | Gln | Arg | Tyr | Asp | Val |      |
|     |     |     | 310 |     |     |     |     | 315 |     |     |     |     | 320 |     |     |      |
| GTC | ATC | GAA | GCC | AAC | CGA | ACG | CCC | GGG | AAC | TAC | TGG | TTT | AAC | GTC | ACA | 1943 |
| Val | Ile | Glu | Ala | Asn | Arg | Thr | Pro | Gly | Asn | Tyr | Trp | Phe | Asn | Val | Thr |      |
|     |     | 325 |     |     |     |     | 330 |     |     |     |     | 335 |     |     |     |      |
| TTT | GGC | GGC | GGC | CTG | CTC | TGC | GGC | GGC | TCC | AGG | AAT | CCC | TAC | CCG | GCC | 1991 |
| Phe | Gly | Gly | Gly | Leu | Leu | Cys | Gly | Gly | Ser | Arg | Asn | Pro | Tyr | Pro | Ala |      |
| 340 |     |     |     |     | 345 |     |     |     |     | 350 |     |     |     |     |     |      |
| GCC | ATC | TTC | CAC | TAC | GCC | GGC | GCC | CCC | GGC | GGC | CCG | CCC | ACG | GAC | GAG | 2039 |
| Ala | Ile | Phe | His | Tyr | Ala | Gly | Ala | Pro | Gly | Gly | Pro | Pro | Thr | Asp | Glu |      |
| 355 |     |     |     |     | 360 |     |     |     |     | 365 |     |     |     |     | 370 |      |
| GGC | AAG | GCC | CCG | GTC | GAC | CAC | AAC | TGC | CTG | GAC | CTC | CCC | AAC | CTC | AAG | 2087 |
| Gly | Lys | Ala | Pro | Val | Asp | His | Asn | Cys | Leu | Asp | Leu | Pro | Asn | Leu | Lys |      |
|     |     |     |     | 375 |     |     |     |     | 380 |     |     |     |     | 385 |     |      |
| CCC | GTC | GTG | GCC | CGC | GAC | GTG | CCC | CTG | AGC | GGC | TTC | GCC | AAG | CGG | GCC | 2135 |
| Pro | Val | Val | Ala | Arg | Asp | Val | Pro | Leu | Ser | Gly | Phe | Ala | Lys | Arg | Ala |      |
|     |     |     | 390 |     |     |     |     | 395 |     |     |     |     | 400 |     |     |      |
| GAC | AAC | ACG | CTC | GAC | GTC | ACC | CTC | GAC | ACC | ACG | GGC | ACG | CCC | CTG | TTC | 2183 |
| Asp | Asn | Thr | Leu | Asp | Val | Thr | Leu | Asp | Thr | Thr | Gly | Thr | Pro | Leu | Phe |      |
|     |     | 405 |     |     |     |     | 410 |     |     |     |     | 415 |     |     |     |      |
| GTC | TGG | AAG | GTC | AAC | GGC | AGC | GCC | ATC | AAC | ATC | GAC | TGG | GGG | AGG | GCC | 2231 |
| Val | Trp | Lys | Val | Asn | Gly | Ser | Ala | Ile | Asn | Ile | Asp | Trp | Gly | Arg | Ala |      |
| 420 |     |     |     |     | 425 |     |     |     |     | 430 |     |     |     |     |     |      |
| GTC | GTC | GAC | TAC | GTC | CTC | ACG | CAG | AAC | ACC | AGC | TTC | CCA | CCC | GGG | TAC | 2279 |
| Val | Val | Asp | Tyr | Val | Leu | Thr | Gln | Asn | Thr | Ser | Phe | Pro | Pro | Gly | Tyr |      |
| 435 |     |     |     |     | 440 |     |     |     |     | 445 |     |     |     |     | 450 |      |
| AAC | ATT | GTC | GAG | GTG | AAC | GGA | GCT | GAT | CAG | GTAAGAAAAA | | GGGGACCGCA | | | | 2329 |
| Asn | Ile | Val | Glu | Val | Asn | Gly | Ala | Asp | Gln |     |     |     |     |     |     |      |
|     |     |     |     | 455 |     |     |     |     | 460 |     |     |     |     |     |     |      |

GGGGTGCTGC TGCAAGTACA CCTTGCTCGC CCTCCTGTTC TTCCTTAATA ACTACCTCCC 2389

AACCCTCCCC CCTAATTAAT TCACTTTAAA GGCCGATCAA GACTGACCGA GCCCCCTCTC 2449

|     |     |     |     |     |     |     |     |     |     |      |
|-----|-----|-----|-----|-----|-----|-----|-----|-----|-----|------|
| TTTGCAG | TGG | TCG | TAC | TGG | TTG | ATC | GAG | AAC | GAT | CCC | GGC | GCA | CCT | TTC | 2498 |
|     | Trp | Ser | Tyr | Trp | Leu | Ile | Glu | Asn | Asp | Pro | Gly | Ala | Pro | Phe |      |
|     |     |     |     |     | 465 |     |     |     |     | 470 |     |     |     |     |      |
| ACC | CTA | CCG | CAT | CCG | ATG | CAC | CTG | CAC | GTAAGTTGGA | | TACATATATA | | | | 2545 |
| Thr | Leu | Pro | His | Pro | Met | His | Leu | His |     |     |     |     |     |     |      |
| 475 |     |     |     |     | 480 |     |     |     |     |     |     |     |     |     |      |

TATATATATA TACATTGCTT TCCTGGCTCG CTCCCTTAAA TAAAATTAAA TAACCAAAAA 2605

TAACAAAAAA AAG GGC CAC GAC TTT TAC GTG CTG GGC CGC TCG CCC GAC 2654

Gly His Asp Phe Tyr Val Leu Gly Arg Ser Pro Asp
485                    490                  495

| | | | | | | | | | | | | | | | | |
|---|---|---|---|---|---|---|---|---|---|---|---|---|---|---|---|---|
| GAG | TCG | CCG | GCA | TCC | AAC | GAG | CGG | CAC | GTG | TTC | GAT | CCG | GCG | CGG | GAC | 2702 |
| Glu | Ser | Pro | Ala | Ser | Asn | Glu | Arg | His | Val | Phe | Asp | Pro | Ala | Arg | Asp | |
| | | | | 500 | | | | 505 | | | | | | 510 | | |
| GCG | GGC | CTG | CTG | AGC | GGG | GCC | AAC | CCT | GTG | CGG | CGG | GAC | GTG | TCG | ATG | 2750 |
| Ala | Gly | Leu | Leu | Ser | Gly | Ala | Asn | Pro | Val | Arg | Arg | Asp | Val | Ser | Met | |
| | | | 515 | | | | | 520 | | | | | 525 | | | |
| CTG | CCG | GCG | TTC | GGG | TGG | GTG | GTG | CTG | TCC | TTC | CGG | GCC | GAC | AAC | CCG | 2798 |
| Leu | Pro | Ala | Phe | Gly | Trp | Val | Val | Leu | Ser | Phe | Arg | Ala | Asp | Asn | Pro | |
| | | 530 | | | | | 535 | | | | | 540 | | | | |
| GGC | GCC | TGG | CTG | TTC | CAC | TGC | CAC | ATC | GCC | TGG | CAC | GTC | TCG | GGC | GGC | 2846 |
| Gly | Ala | Trp | Leu | Phe | His | Cys | His | Ile | Ala | Trp | His | Val | Ser | Gly | Gly | |
| | 545 | | | | | 550 | | | | | 555 | | | | | |
| CTG | GGC | GTC | GTC | TAC | CTC | GAG | CGC | GCC | GAC | GAC | CTG | CGC | GGG | GCC | GTC | 2894 |
| Leu | Gly | Val | Val | Tyr | Leu | Glu | Arg | Ala | Asp | Asp | Leu | Arg | Gly | Ala | Val | |
| 560 | | | | | 565 | | | | | 570 | | | | | 575 | |
| TCG | GAC | GCC | GAC | GCC | GAC | GAC | CTC | GAC | CGC | CTC | TGC | GCC | GAC | TGG | CGC | 2942 |
| Ser | Asp | Ala | Asp | Ala | Asp | Asp | Leu | Asp | Arg | Leu | Cys | Ala | Asp | Trp | Arg | |
| | | | | 580 | | | | | 585 | | | | | 590 | | |
| CGC | TAC | TGG | CCT | ACC | AAC | CCC | TAC | CCC | AAG | TCC | GAC | TCG | GGC | CTC | AAA | 2990 |
| Arg | Tyr | Trp | Pro | Thr | Asn | Pro | Tyr | Pro | Lys | Ser | Asp | Ser | Gly | Leu | Lys | |
| | | | 595 | | | | | 600 | | | | | 605 | | | |
| CAC | CGC | TGG | GTC | GAG | GAG | GGC | GAG | TGG | CTG | GTC | AAG | GCG | TGAGCGAAGG | | | 3039 |
| His | Arg | Trp | Val | Glu | Glu | Gly | Glu | Trp | Leu | Val | Lys | Ala | | | | |
| | | 610 | | | | | 615 | | | | 620 | | | | | |

AGGAAAAAGG AAACAAAGAG GGGGGGGGGG GCTAGTTCCT ATTTTTGCTT TTTTTTTTG 3099

TTCTTGTCCT TGTGCTGGCG GTTCCCTGGT AAAGGAGAAG GGGGCCCCAA GTTCGAGTGG 3159

GTGTGTGATC GGGTAAATAT TATCAAGAGA TCT 3192

(2) INFORMATION FOR SEQ ID NO:27:

(i) SEQUENCE CHARACTERISTICS:
        (A) LENGTH: 620 amino acids
        (B) TYPE: amino acid
        (D) TOPOLOGY: linear (ii) MOLECULE TYPE: protein (xi) SEQUENCE DESCRIPTION: SEQ ID NO:27:

| | | | | | | | | | | | | | | |
|---|---|---|---|---|---|---|---|---|---|---|---|---|---|---|
| Met | Lys | Ser | Phe | Ile | Ser | Ala | Ala | Thr | Leu | Leu | Val | Gly | Ile | Leu | Thr |
| 1 | | | | 5 | | | | | 10 | | | | | 15 | |
| Pro | Ser | Val | Ala | Ala | Ala | Pro | Pro | Ser | Thr | Pro | Glu | Gln | Arg | Asp | Leu |
| | | | 20 | | | | | 25 | | | | | 30 | | |
| Leu | Val | Pro | Ile | Thr | Glu | Arg | Glu | Ala | Ala | Val | Lys | Ala | Arg | Gln | |
| | | | 35 | | | | | 40 | | | | | 45 | | |
| Gln | Ser | Cys | Asn | Thr | Pro | Ser | Asn | Arg | Ala | Cys | Trp | Thr | Asp | Gly | Tyr |
| | 50 | | | | | 55 | | | | | 60 | | | | |
| Asp | Ile | Asn | Thr | Asp | Tyr | Glu | Val | Asp | Ser | Pro | Asp | Thr | Gly | Val | Val |
| 65 | | | | | 70 | | | | | 75 | | | | | 80 |
| Arg | Pro | Tyr | Thr | Leu | Thr | Leu | Thr | Glu | Val | Asp | Asn | Trp | Thr | Gly | Pro |
| | | | | 85 | | | | | 90 | | | | | 95 | |
| Asp | Gly | Val | Val | Lys | Glu | Lys | Val | Met | Leu | Val | Asn | Asn | Ser | Ile | Ile |
| | | | 100 | | | | | 105 | | | | | 110 | | |
| Gly | Pro | Thr | Ile | Phe | Ala | Asp | Trp | Gly | Asp | Thr | Ile | Gln | Val | Thr | Val |
| | | 115 | | | | | 120 | | | | | 125 | | | |
| Ile | Asn | Asn | Leu | Glu | Thr | Asn | Gly | Thr | Ser | Ile | His | Trp | His | Gly | Leu |
| | | 130 | | | | | 135 | | | | | 140 | | | |
| His | Gln | Lys | Gly | Thr | Asn | Leu | His | Asp | Gly | Ala | Asn | Gly | Ile | Thr | Glu |
| 145 | | | | | 150 | | | | | 155 | | | | | 160 |

```
Cys  Pro  Ile  Pro  Pro  Lys  Gly  Gly  Arg  Lys  Val  Tyr  Arg  Phe  Lys  Ala
               165                 170                           175

Gln  Gln  Tyr  Gly  Thr  Ser  Trp  Tyr  His  Ser  His  Phe  Ser  Ala  Gln  Tyr
               180                 185                           190

Gly  Asn  Gly  Val  Val  Gly  Ala  Ile  Gln  Ile  Asn  Gly  Pro  Ala  Ser  Leu
               195                 200                           205

Pro  Tyr  Asp  Thr  Asp  Leu  Gly  Val  Phe  Pro  Ile  Ser  Asp  Tyr  Tyr  Tyr
     210                      215                           220

Ser  Ser  Ala  Asp  Glu  Leu  Val  Glu  Leu  Thr  Lys  Asn  Ser  Gly  Ala  Pro
225                 230                      235                           240

Phe  Ser  Asp  Asn  Val  Leu  Phe  Asn  Gly  Thr  Ala  Lys  His  Pro  Glu  Thr
               245                      250                           255

Gly  Glu  Gly  Glu  Tyr  Ala  Asn  Val  Thr  Leu  Thr  Pro  Gly  Arg  Arg  His
               260                      265                           270

Arg  Leu  Arg  Leu  Ile  Asn  Thr  Ser  Val  Glu  Asn  His  Phe  Gln  Val  Ser
               275                      280                      285

Leu  Val  Asn  His  Thr  Met  Cys  Ile  Ile  Ala  Ala  Asp  Met  Val  Pro  Val
     290                      295                      300

Asn  Ala  Met  Thr  Val  Asp  Ser  Leu  Phe  Leu  Gly  Val  Gly  Gln  Arg  Tyr
305                      310                      315                      320

Asp  Val  Val  Ile  Glu  Ala  Asn  Arg  Thr  Pro  Gly  Asn  Tyr  Trp  Phe  Asn
               325                      330                           335

Val  Thr  Phe  Gly  Gly  Gly  Leu  Leu  Cys  Gly  Gly  Ser  Arg  Asn  Pro  Tyr
               340                      345                      350

Pro  Ala  Ala  Ile  Phe  His  Tyr  Ala  Gly  Ala  Pro  Gly  Gly  Pro  Pro  Thr
               355                      360                      365

Asp  Glu  Gly  Lys  Ala  Pro  Val  Asp  His  Asn  Cys  Leu  Asp  Leu  Pro  Asn
     370                      375                      380

Leu  Lys  Pro  Val  Val  Ala  Arg  Asp  Val  Pro  Leu  Ser  Gly  Phe  Ala  Lys
385                      390                      395                      400

Arg  Ala  Asp  Asn  Thr  Leu  Asp  Val  Thr  Leu  Asp  Thr  Thr  Gly  Thr  Pro
               405                      410                           415

Leu  Phe  Val  Trp  Lys  Val  Asn  Gly  Ser  Ala  Ile  Asn  Ile  Asp  Trp  Gly
               420                      425                      430

Arg  Ala  Val  Val  Asp  Tyr  Val  Leu  Thr  Gln  Asn  Thr  Ser  Phe  Pro  Pro
               435                      440                      445

Gly  Tyr  Asn  Ile  Val  Glu  Val  Asn  Gly  Ala  Asp  Gln  Trp  Ser  Tyr  Trp
     450                      455                      460

Leu  Ile  Glu  Asn  Asp  Pro  Gly  Ala  Pro  Phe  Thr  Leu  Pro  His  Pro  Met
465                      470                      475                      480

His  Leu  His  Gly  His  Asp  Phe  Tyr  Val  Leu  Gly  Arg  Ser  Pro  Asp  Glu
               485                      490                      495

Ser  Pro  Ala  Ser  Asn  Glu  Arg  His  Val  Phe  Asp  Pro  Ala  Arg  Asp  Ala
               500                      505                      510

Gly  Leu  Leu  Ser  Gly  Ala  Asn  Pro  Val  Arg  Arg  Asp  Val  Ser  Met  Leu
          515                      520                      525

Pro  Ala  Phe  Gly  Trp  Val  Val  Leu  Ser  Phe  Arg  Ala  Asp  Asn  Pro  Gly
     530                      535                      540

Ala  Trp  Leu  Phe  His  Cys  His  Ile  Ala  Trp  His  Val  Ser  Gly  Gly  Leu
545                      550                      555                      560

Gly  Val  Val  Tyr  Leu  Glu  Arg  Ala  Asp  Asp  Leu  Arg  Gly  Ala  Val  Ser
               565                      570                      575

Asp  Ala  Asp  Ala  Asp  Asp  Leu  Asp  Arg  Leu  Cys  Ala  Asp  Trp  Arg  Arg
```

```
                      580                       585                              590
Tyr  Trp  Pro  Thr  Asn  Pro  Tyr  Pro  Lys  Ser  Asp  Ser  Gly  Leu  Lys  His
          595                      600                      605

Arg  Trp  Val  Glu  Glu  Gly  Glu  Trp  Leu  Val  Lys  Ala
     610                 615                      620
```

(2) INFORMATION FOR SEQ ID NO:28:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

```
Ile  Asp  Trp  His  Val  Ser  Gly  Gly  Leu  Ala  Leu
1                      5                      10
```

(2) INFORMATION FOR SEQ ID NO:29:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

```
Leu  Glu  Ala  Gly  Phe  Ala  Leu  Val
1                      5
```